(12) United States Patent
Arai et al.

(10) Patent No.: US 6,897,054 B1
(45) Date of Patent: May 24, 2005

(54) HUMAN H37 PROTEINS AND CDNA ENCODING THE SAME

(75) Inventors: Kenichi Arai, Tokyo (JP); Hisao Masai, Tokyo (JP)

(73) Assignee: Japan Science and Technology Agency, Kawaguchi (JP)

( * ) Notice: Subject to any disclaimer, the term of this patent is extended or adjusted under 35 U.S.C. 154(b) by 0 days.

(21) Appl. No.: 09/830,647

(22) PCT Filed: Nov. 1, 1999

(86) PCT No.: PCT/JP99/06076

§ 371 (c)(1),
(2), (4) Date: Jul. 30, 2001

(87) PCT Pub. No.: WO00/26250

PCT Pub. Date: May 11, 2000

(30) Foreign Application Priority Data

Oct. 30, 1998 (JP) ............................................ 10-311408

(51) Int. Cl.$^7$ .......................... C12N 9/12; C07K 16/00; C07K 14/00; C07K 17/00; C12P 21/08
(52) U.S. Cl. ............... 435/194; 530/388.24; 530/389.2; 530/350; 530/358; 536/23.1; 536/24.3
(58) Field of Search ..................... 435/194; 530/388.24, 530/389.2, 350, 358; 536/23.1, 24.3

(56) References Cited

FOREIGN PATENT DOCUMENTS

WO   WO200058473 A2 * 10/2000
WO   WO200157278 A2 *  8/2001

OTHER PUBLICATIONS

Kumagai H, Sato N, Yamada M, Mahony D, Seghezzi W, Lees E, Arai K, Masai H. A novel growth– and cell cycle–regulated protein, ASK, activates human Cdc7–related kinase and is essential for G1/S transition in mammalian cells. Mol Cell Biol. Jul. 1999;19(7).*
Molecular and Cellular Biology, vol. 19, No. 7, issued Jul. 1999, Hiroyuki Kumagai et al., "A Novel Growth– and Cell Cycle– Regulated Protein, ASK, Activates Human Cdc7–Related Kinase and is Essential for G1/S Transition Mammalian Cells", pp. 5083–5095.
Database MEDLINE on PubMed, Accession No. 10523313, Jiang, W. et al., "Mammalian Cdc7–Dbf4 protein kinase complex is essential for initiation of DNA replication", EMBO Journal, vol. 18, No. 20, issued 15 Oct. 1999, pp. 5703–5713.
Database GenBank, Accession No. AF160876, Jul. 22, 1999, Hollingsworth, R., "Homo sapiens DBF4–like protein (DBF4) mRNA, complete cds.".
The Journal of Biological Chemistry, vol. 273, No. 36, issued Sep. 4, 1998, Jung Min Kim et al., "Growth Regulation of the Expression of Mouse cDNA and Gene Encoding a Serine/Threonine Kinase Related to Saccharomyces cerevisiae CDC7 Essential for G1/S Transition", pp. 23248–23257.
Proceedings of the National Academy of Sciences, USA, vol. 94, No. 26, issued Dec. 23, 1997, Wei Jiang et al., "Identification and Characterization of a human protein kinase related to budding yeast Cdc7p", pp. 14320–14325.
The EMBO Journal, vol. 16, No. 14, issued Jul. 16, 1997, Noriko Sato et al., "Human and Xenopus cDNAs encoding budding yeast Cdc7–related kinases: in vitro phosphorylation of MCM subunits by a putative human homologue of Cdc7", pp. 4340–4351.

* cited by examiner

Primary Examiner—Gary Nickol
Assistant Examiner—Christopher Yaen
(74) Attorney, Agent, or Firm—Wenderoth, Lind & Ponack, L.L.P.

(57) ABSTRACT

This application provides human H37 protein having an amino acid sequence of SEQ ID NO: 1 or NO: 2; human gene encoding the protein; cDNA of the human gene which has a base sequence of SEQ ID NO: 3 or NO: 4; DNA fragment comprising a partial sequence of the cDNA; recombinant vector having the cDNA; antibody against human H37 protein; and a method for controlling the proliferation of cells by introducing the above DNA or antibody into the cells.

26 Claims, 20 Drawing Sheets

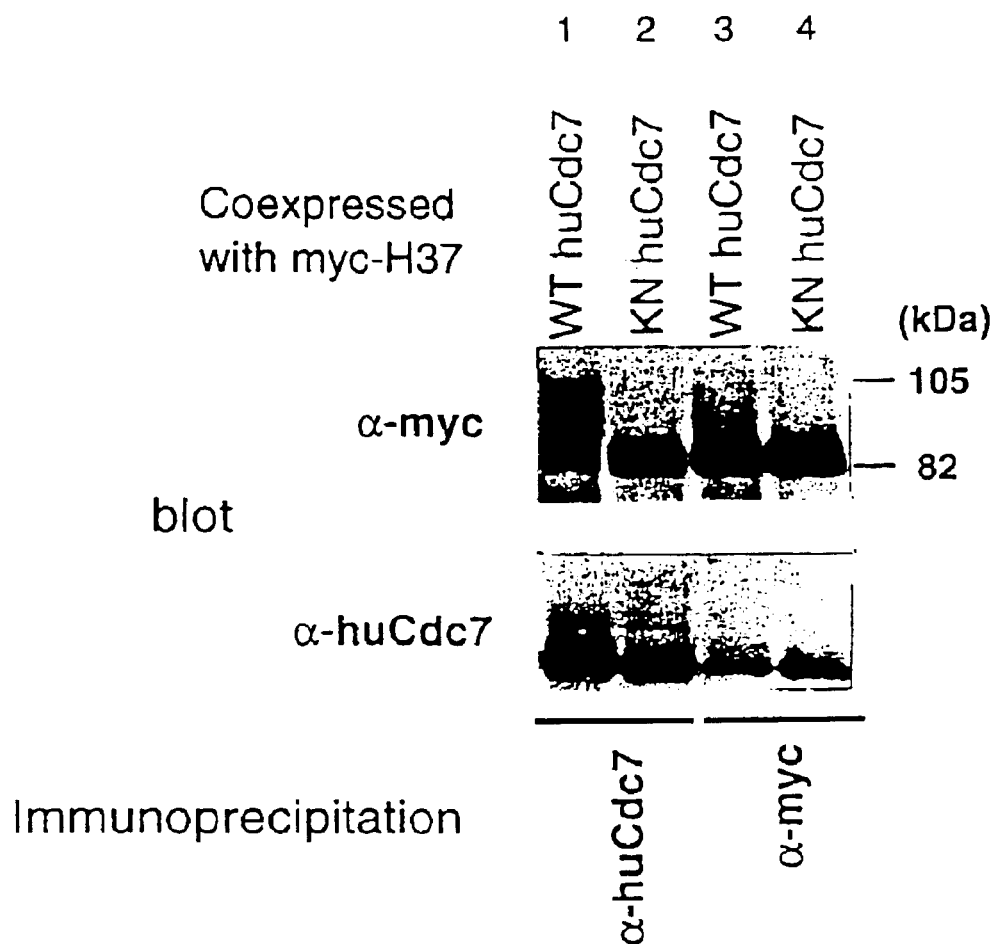

Fig. 5

```
1         10        20        30        40        50        60
MNSGAMRIHSKGHFQGGIQVKNEKNRPSLKSLKTDNRPEKSKCKPLWGKVFYLDLPSVTI
                              Dbf4 motif-N
61        70        80        90        100       110       120
SEKLQKDIKDLGGRVEEFLSKDISYLISNKKEAKFAQTLGRISPVPSPESAYTAETTSPH 121       130       140       150       160       170       180
PSHDGSSFKSPDTVCLSRGKLLVEKAIKDHDFIPSNSILSNALSWGVKILHIDDIRYYIE 181       190       200       210       220       230       240
QKKKELYLLKKSSTSVRDGGKRVGSGAQKTRTGRLKKPFVKVEDMSQLYRPFYLQLTNMP 241       250       260       270       280       290       300
FINYSIQKPCSPFDVDKPSSMQKQTQVKLRIQTDGDKYGGTSIQLQLKEKKKKGYCECCL
                         Dbf4 motif-C
301       310       320       330       340       350       360
QKYEDLETHLLSEQHRNFAQSNQYQVVDDIVSKLVFDFVEYEKDTPKKKRIKYSVGSLSP 361       370       380       390       400       410       420
VSASVLKKTEQKEKVELQHISQKDCQEDDTTVKEQNFLYKETQETEKKLLFISEPIPHPS 421       430       440       450       460       470       480
NELRGLNEKMSNKCSMLSTAEDDIRQNFTQLPLHKNKQECILDISEHTLSENDLEELRVD 481       490       500       510       520       530       540
HYKCNIQASVHVSDFSTDNSGSQPKQKSDTVLFPAKDLKEKDLHSIFTHDSGLITINSSQ 541       550       560       570       580       590       600
EHLTVQAKAPFHTPPEEPNECDFKNMDSLPSGKIHRKVKIILGRNRKENLEPNAEFDKRT 601       610       620       630       640       650       660
EFITQEENRICSSPVQSLLDLFQTSEEKSEFLGFTSYTEKSGICNVLDIWEEENSDNLLT 661       670  674
AFFSPSTSTFTGF*
```

Fig. 14
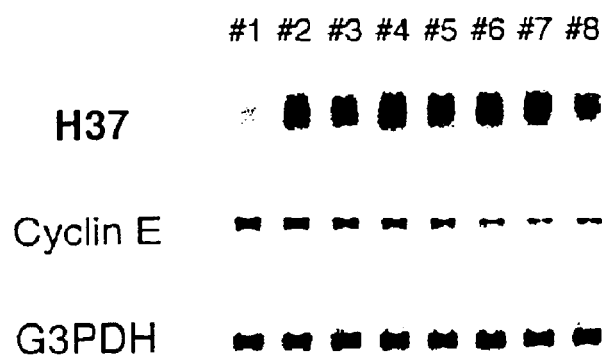
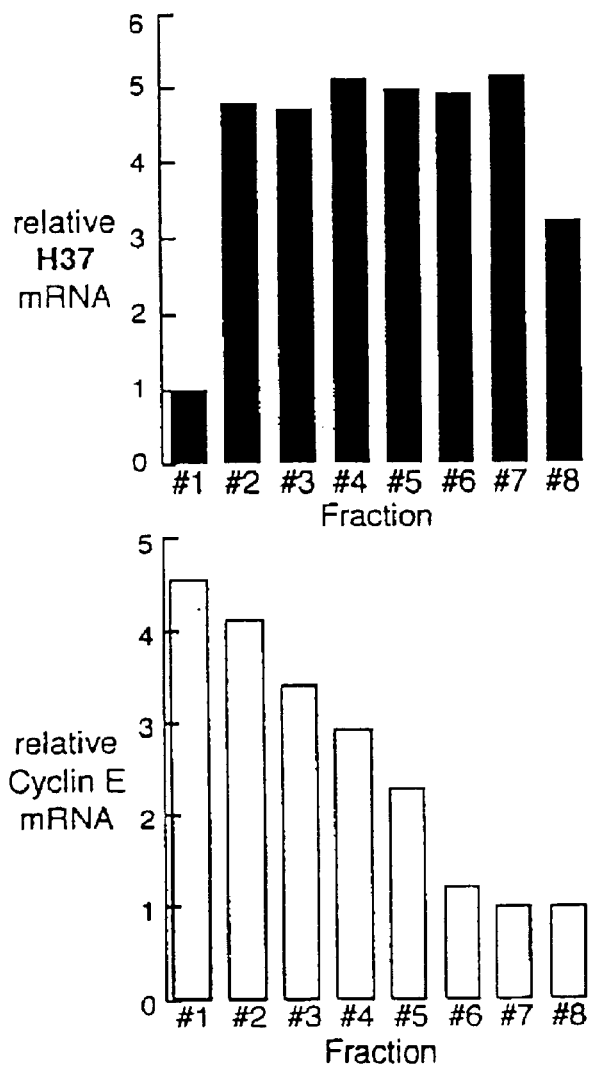

Fig.17
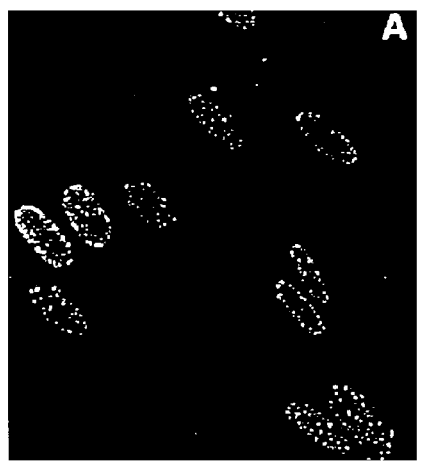
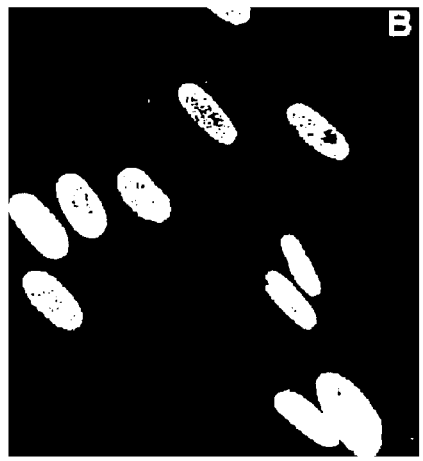
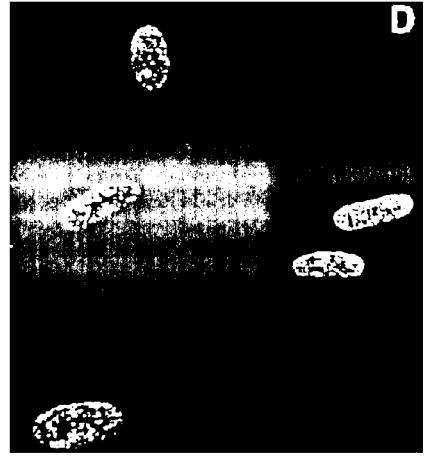
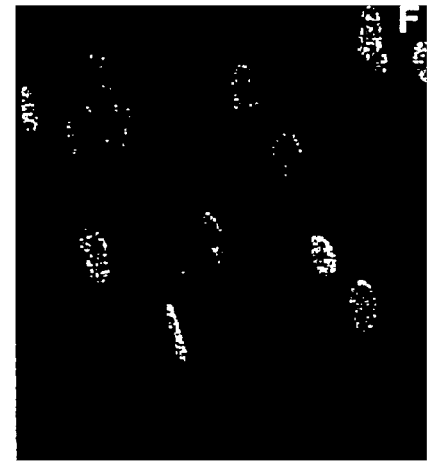

HUMAN H37 PROTEINS AND CDNA ENCODING THE SAME

BACKGROUND OF THE INVENTION

1. Field of the Invention

This application relates to human H37 protein and to cDNA encoding the protein. More particularly, this application relates to human H37 protein that is an activity-controlling subunit for the protein Cdc7 controlling the replication of human cells; to human gene encoding the protein; to an antibody to the H37 protein; and to a method for controlling the proliferation of human cells using such genetic engineering material and antibody.

2. Description of the Related Art

Proliferation of cells is initiated when a liquid factor called a growth factor is bound to the receptor on the cell surface and a signal for proliferation is transmitted into the cell. Accordingly, for an artificial induction of proliferation of incubated cells, methods where an excessive amount of a growth factor is added to a cell medium, where a receptor which is not inherently owned by the said cell is expressed on the cell surface and a factor which is specific for the receptor is added to a medium, etc. have been carried out. Further, in suppressing the cell proliferation, methods where competing molecule, antagonist or the like to the receptor protein is added to the medium to suppress the binding of the receptor to the growth factor, etc. have been carried out.

On the other hand, in the case of the cell where a proliferation signal is issued by binding of the receptor to the growth factor, a cycle in which its genomic DNA is replicated, uniformly distributed to daughter cells and then divided is repeated. Such a cycle is called "cell cycle" especially for eukaryotes. The cell cycle is basically classified into four phases. Thus, S phase when chromosomal DNA is replicated; M phase when the replicated chromosome is divided by a spindle body and then cytoplasm is divided; G1 phase which is a period from M phase finishes until S phase begins; and G2 phase which is a period from S phase finishes until M phase starts. Transition from G1 phase to S phase is particularly strictly controlled and DNA replication takes place only once in S phase.

It has been confirmed from the studies in yeast and higher eukaryotic cells that cyclin-dependent kinase plays a critical role in the cell cycle progression (Nature 292:558–560, 1981; Cell 66:731–742, 1991; Nature 349:338393, 1991; Science 257:1958–1961, 1992; Bioassays 17:471, 1995). Further, from a genetic analysis in yeast, it has been clarified that another serine/threonine linase plays an essential role in the initial stage of S phase (G1/S transition). Thus, characterization of cdc7 mutation which was isolated as one of the cell division cycle mutants (J. Mol. Biol. 59:183–194, 1971), it revealed that the Cdc7 protein kinase functions immediately prior to chromosomal replication and that, during S phase, that is necessary for activation of origins (Mol. Cell Biol. 6:1590–1598, 1986; Genes Dev. 15:480–490, 1998; Genes Dev. 15:491–501, 1998). It has been also clarified that the Cdc7 kinase activity is dependent upon the presence of a regulatory subunit, Dbf4 (Genetics 131:21–29, 1992; Mol. Cell. Biol. 13:2899–2908, 1993). Expression of Dbf4 is periodic and is regulated by both at the transcriptional and post-translational levels (Exp. Cell Res. 180:419–428, 1989). The increase in Cdc7 kinase activity at the G1/S boundary is at least accounted for by the elevated expression of Dbf4 in late G1 phase (Mol. Cell. Biol. 13:2899–2908, 1994; Exp. Cell Res. 180:419–428, 1989). In addition, since Dbf4 interacts with replication origins in vivo (Science 265:1243–1246, 1994), it has been suggested that the Cdc7 may trigger S phase by directly activating the replication initiation complex assembled at the origins.

In addition, the inventors of this application had already isolated kinases related to yeast Cdc7 from *Schizosaccharomyces prombe*, Xenopus, mouse and human (J. Biol. Chem. 273:23248–23257, 1998; EMBO J. 16:4340–4351, 1997; EMBO J. 14:3094–3104, 1995), and pointed out that eukaryotic chromosomal replication is regulated by a conserved mechanism involving this family of kinase.

From the findings in yeast and higher eukaryotes as mentioned above, it is expected that an artificial control of the cell proliferation is possible by means of the regulation of the Cdc7 kind activity in cells, which is entirely other means than conventional methods using operation of growth factor/receptor binding.

However, the inventors had also found that the putative human homolog of Cdc7, huCdc7, possesses only a very low level of kinase activity when overexpressed in mammalian cells while a baculovirus expressed form of huCdc7 is inactive.

Under such circumstances, the inventors of this application have investigated a human cDNA library with a presumption of the presence of a regulatory subunit for human Cdc7, succeeded in isolating the cDNA encoding a novel protein which regulates the kinase activity by binding to huCdc7 and named the said protein encoded in this cDNA as H37 protein.

An object of the invention is to provide the novel protein obtained by the inventors in an industrial applicable form.

Another object of the invention is to provide a human gene encoding the protein and to provide a material for genetic operation including cDNA derived from the gene, an antibody to the protein.

Still another object of the invention is to provide a method for the artificial control of proliferation of human cells using the above material for genetic operation.

SUMMARY OF THE INVENTION

This application provides human H37 protein having an amino acid sequence of SEQ ID NO: 1 or NO: 2.

This application also provides human H37 protein having an amino acid sequence where one or more amino acid residue(s) in the amino acid sequence of SEQ ID NO: 1 or NO: 2 is/are deleted therefrom, substituted therefor or added thereto.

This application further provides a human gene encoding the above-mentioned human H37 protein; cDNA of said human gene which has a base sequence of SEQ ID NO: 3 or NO: 4; and DNA fragment comprising a partial sequence of those cDNAs.

This application furthermore provides a recombinant vector having the above-mentioned cDNA and an antibody against the human H37 protein.

This application still further provides a method for promoting the proliferation of cells, which comprises introducing the above-mentioned cDNA or the DNA fragment together with expression regulatory sequence into cell, and a method for suppressing the proliferation of cells, which comprises introducing the above-mentioned antibody into the cell.

BRIEF DESCRIPTION OF THE DRAWINGS

FIG. 4 shows mobility shift of H37 induced by coexpression of wild-type huCdc7. Extracts were prepared from Cos7 cells expressing either wild-type or kinase negative huCdc7 together with myc-tagged H37. Immmunoprecipitates with anti-huCdc7 antibody No. 1 (lanes 1 and 2) or anti-myc antibody (lanes 3 and 4) were blotted with anti-myc antibody (upper) or anti-huCdc7 antibody (lower). In all cases, samples were run on 8% SDS-PAGE.

FIG. 5 shows an amino acid sequence of the full-length H37 protein which is as same as the SEQ ID NO: 1.

Appendix A

Figure 6:
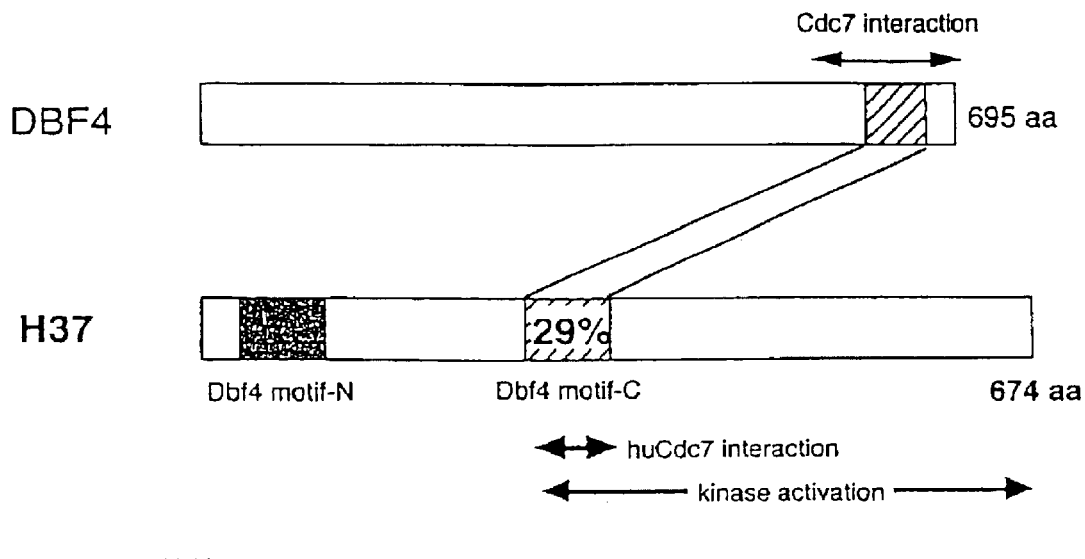
FIG. 6 shows schematic representation of conserved regions between Dbf4 and H37. The double-arrowed region on Dbf4 was reported to be sufficient for interaction with huCdc7. Solid and gray double-arrowed region on H37 indicates the portion essential for interaction with huCdc7 or that sufficient for activation of huCdc7 kinase activity, respectively.

Dbf4 motif-N of Human H37 ("H37" and "huDbf4N") protein shown in FIG. 6 corresponds to position 32–98 SEQ ID No: 1 of the Sequence Listing. Dbf4 motif-N of Mouse H37 ("mu-H37" and "muDbf4N") protein shown in FIG. 6 corresponds to SEQ ID No: 5. Dbf4 motif-N of Fruit Fly H37 ("Dm-H37" and "DmDbf4N") protein shown in FIG. 6 corresponds to SEQ ID No: 6. Dbf4 motif-C of Human H37 ("H37") protein corresponds to postions 263–322 of SEQ ID No: 1. Dbf4 motif-C of Mouse H37 ("mu-H37") protein corresponds to SEQ ID No. 7. Dbf4 motif-C of Fruit Fly H37 ("Dm-H37") protein corresponds to SEQ ID No: 8. Dbf4 motif-C of Budding Yeast ("Dbf4") corresponds to SEQ ID No:9.

Figure 7:
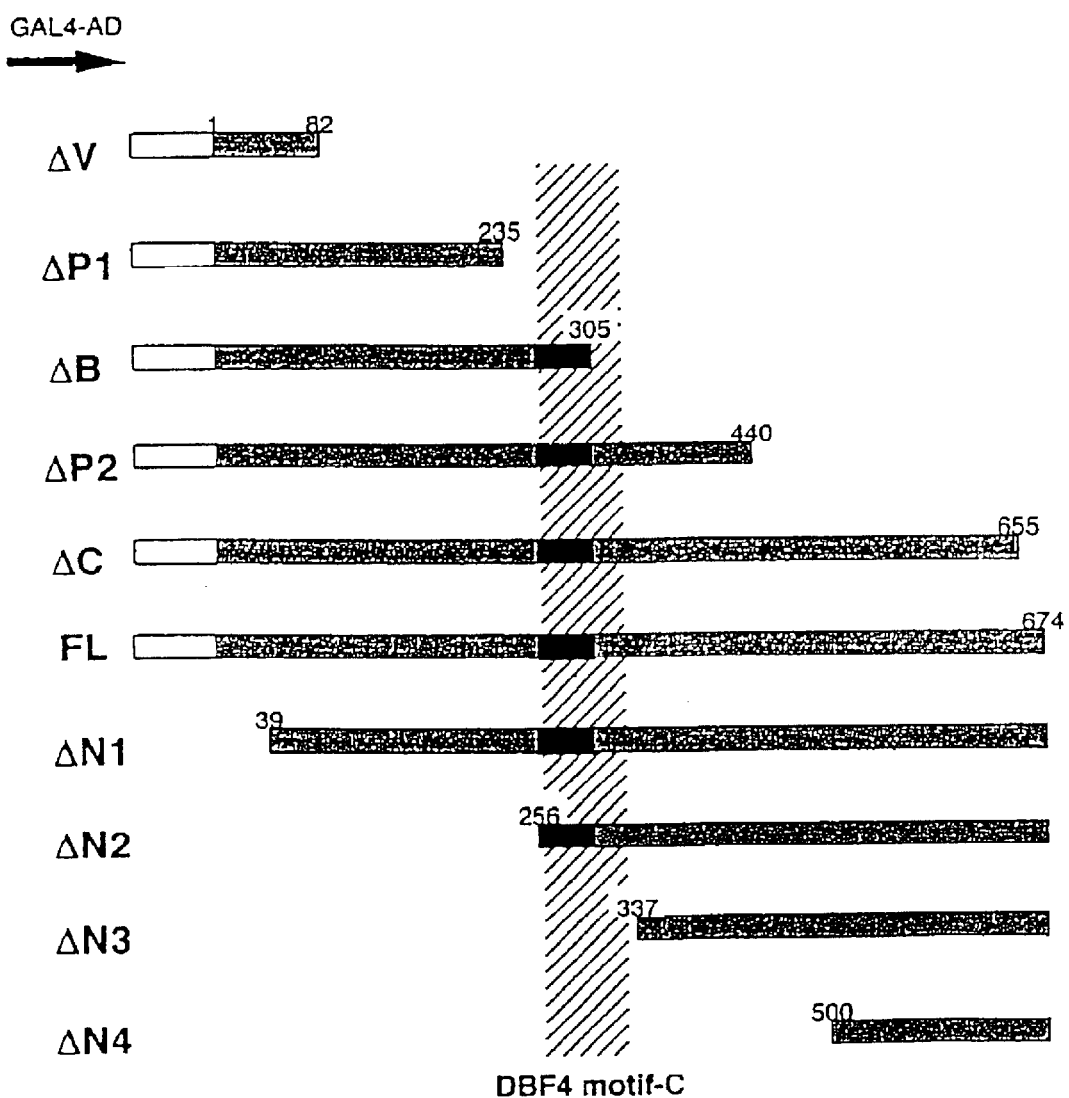

FIG. 7 is a schematic representation of N-terminal and C-terminal deletion derivatives of H37 proteins. The number at the end of each bar indicates the portion of the amino acid (corresponding to SEQ ID NO: 1) at the deletion endpoint. The striped region indicates Dbf4 motif-C.

Figure 8:
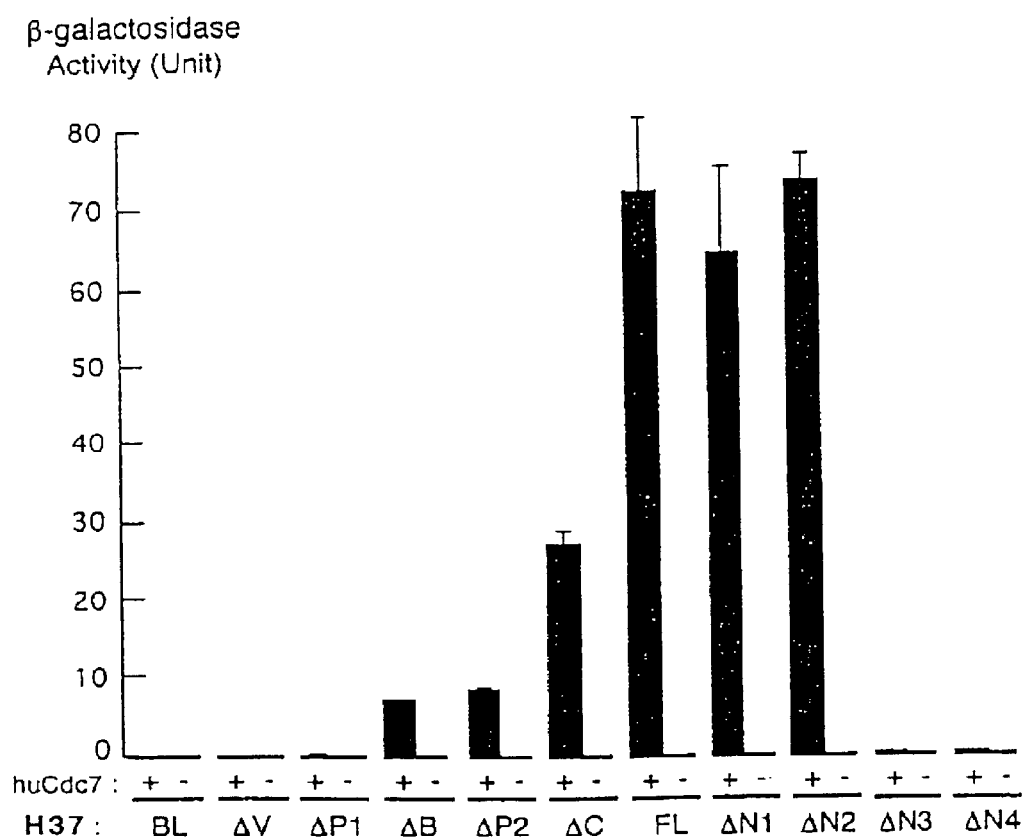

FIG. 8 shows lacZ activity of H37 deletion derivatives in two-hybrid assay with huCdc7.

Figure 9:
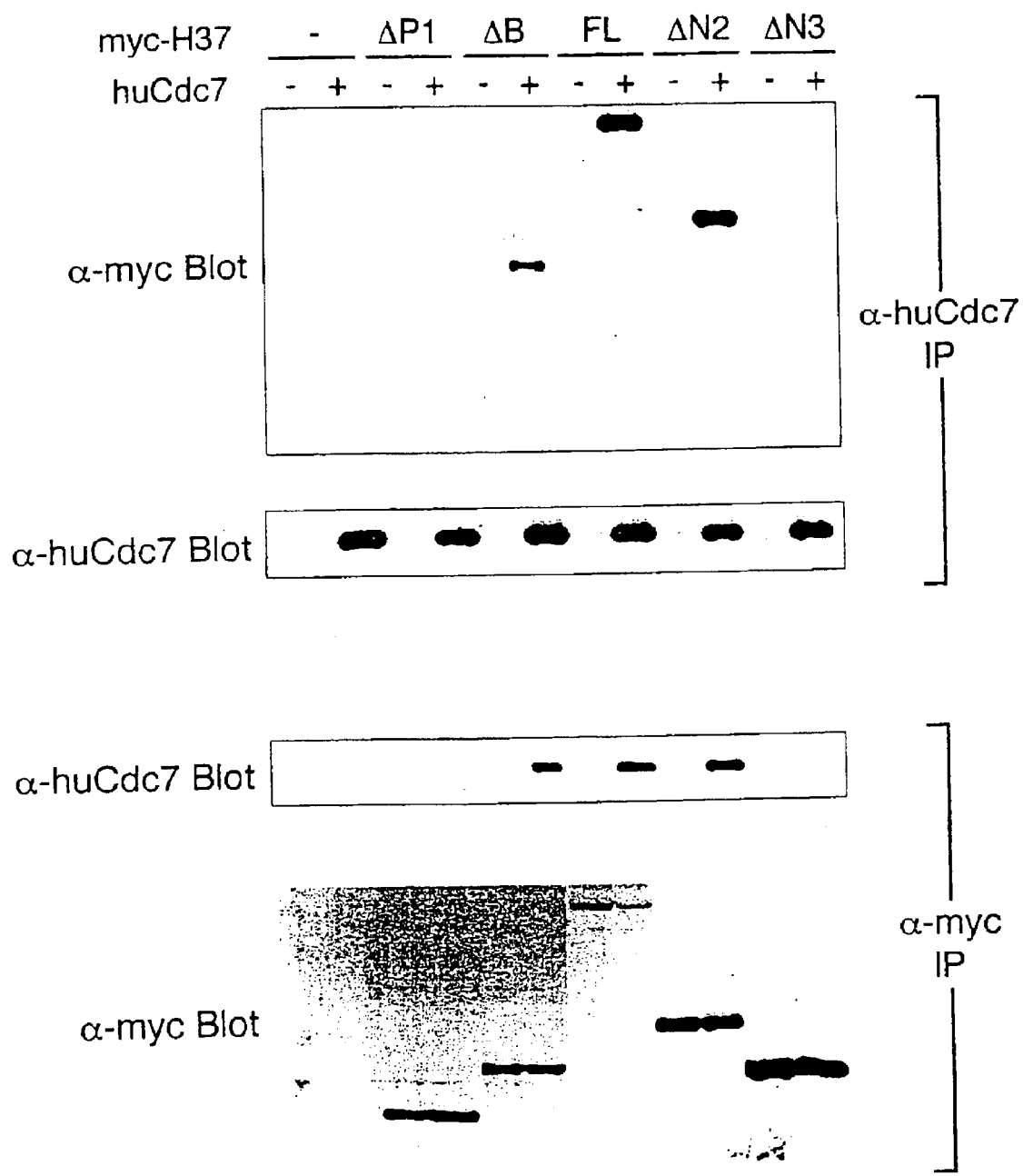

FIG. 9 shows the result of antibody coprecipitation method in which H37 deletion derivatives and huCdc7 were co-expressed in COS7 cells and a complex formation was measured.

Figure 10:
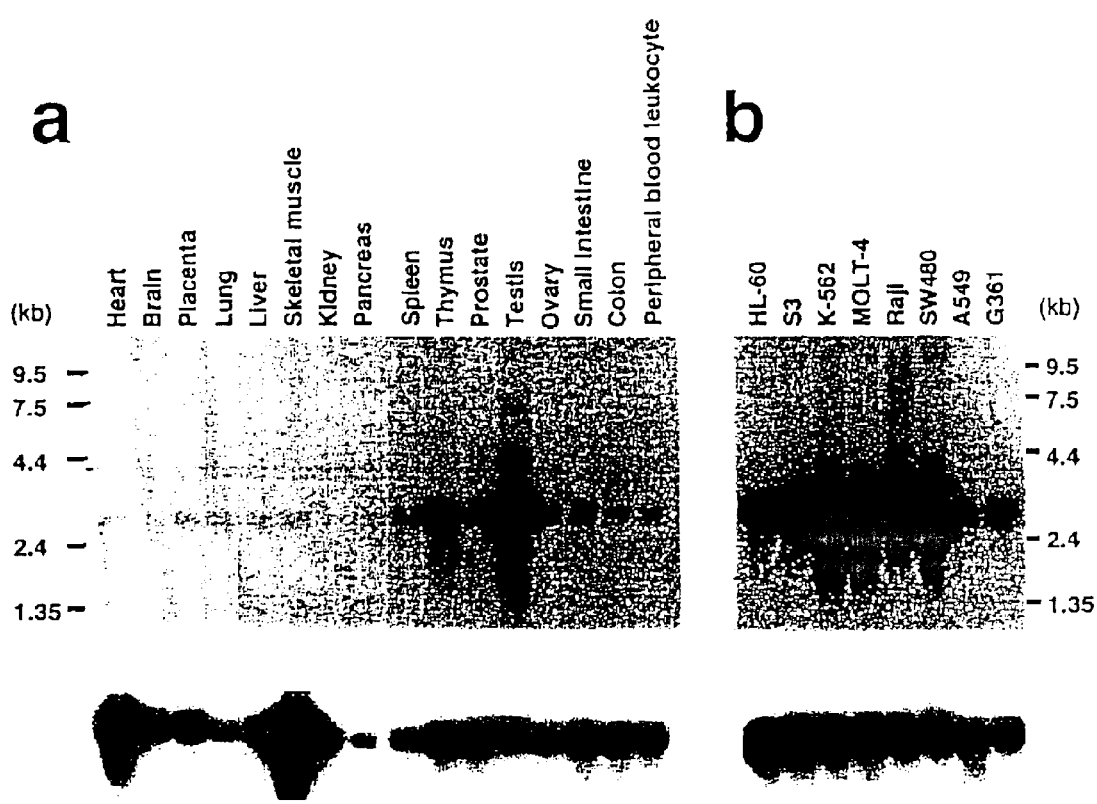

FIG. 10($a$) is the result of northern analysis of H37 mRNA expression in various tissues, and ($b$) is the result of a northern analysis of H37 mRNA expression in various cancer cell lines.

Figure 11:
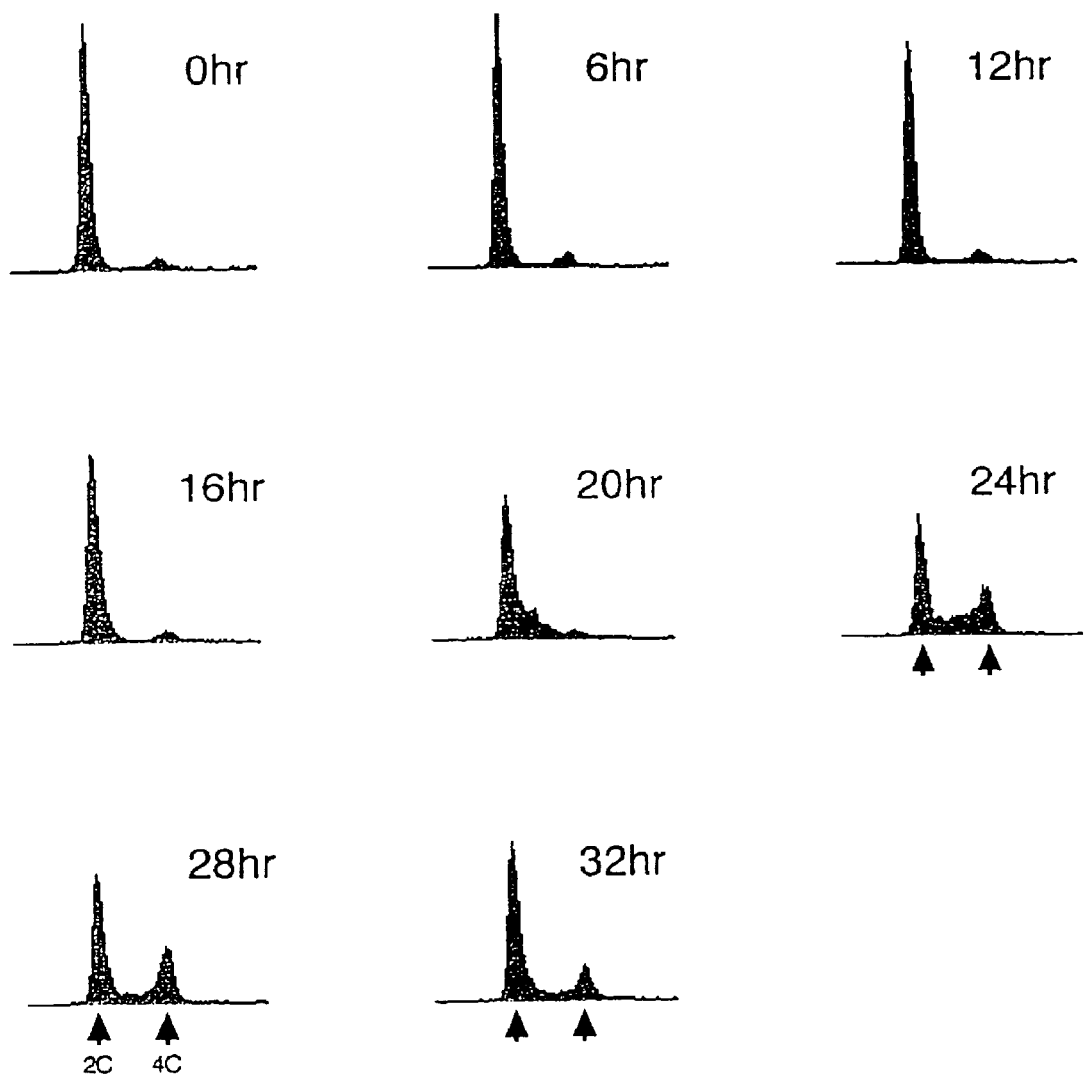

FIG. 11 shows the results where WI38 cells in a resting phase are stimulated by addition of 10% of serum and DNA contents at various stages were analyzed by means of FACS.

Figure 12:
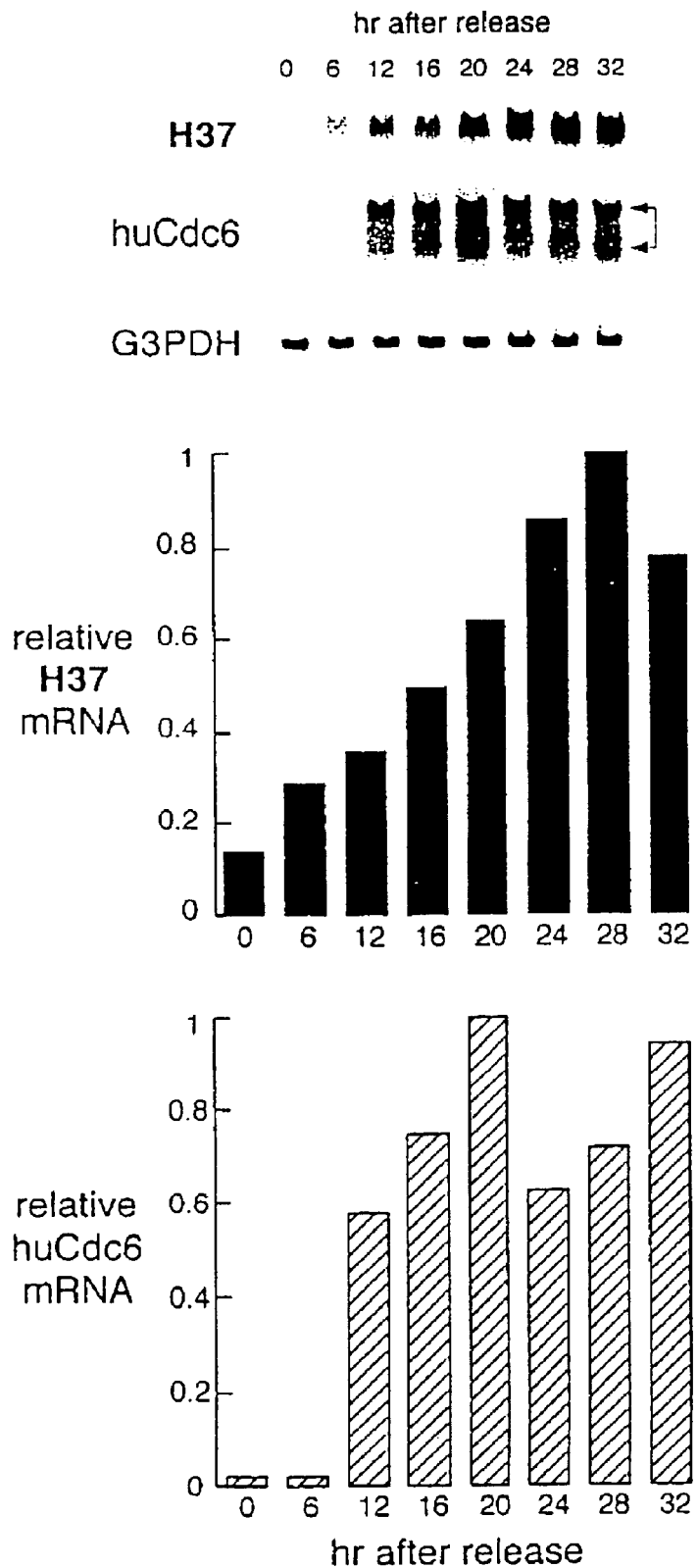

FIG. 12 shows the result of northern analysis of H37 and huCdc6 expression by using RNA extracted from cells of FIG. 11 (upper), and the graphs showing the relative expression amount of each mRNA (middle and lower).

Figure 13:
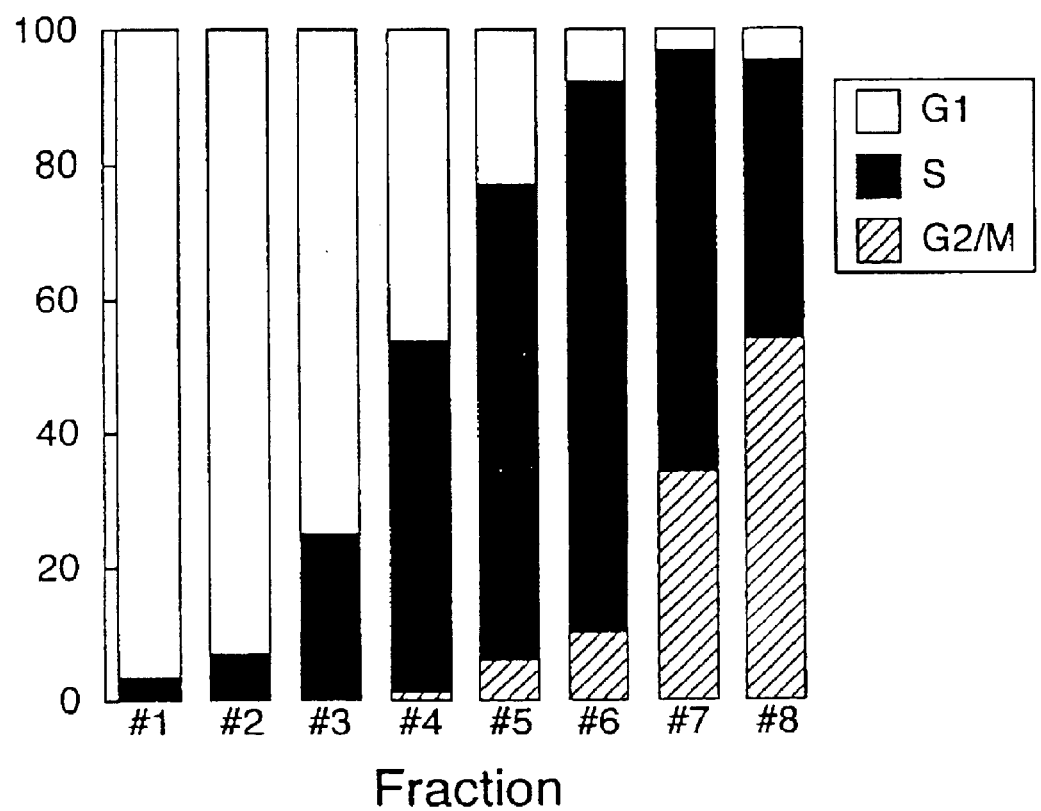

FIG. 13 shows graphs showing each cell cycle fraction of human CEM cells fractionated by an elutriation method.

FIG. 14 shows the result of northern analysis for expression of H37 and cyclin E in each fraction of FIG. 13 (upper), and also shows the graphs showing the relative expression amounts of each mRNA (middle and lower).

Figure 15:
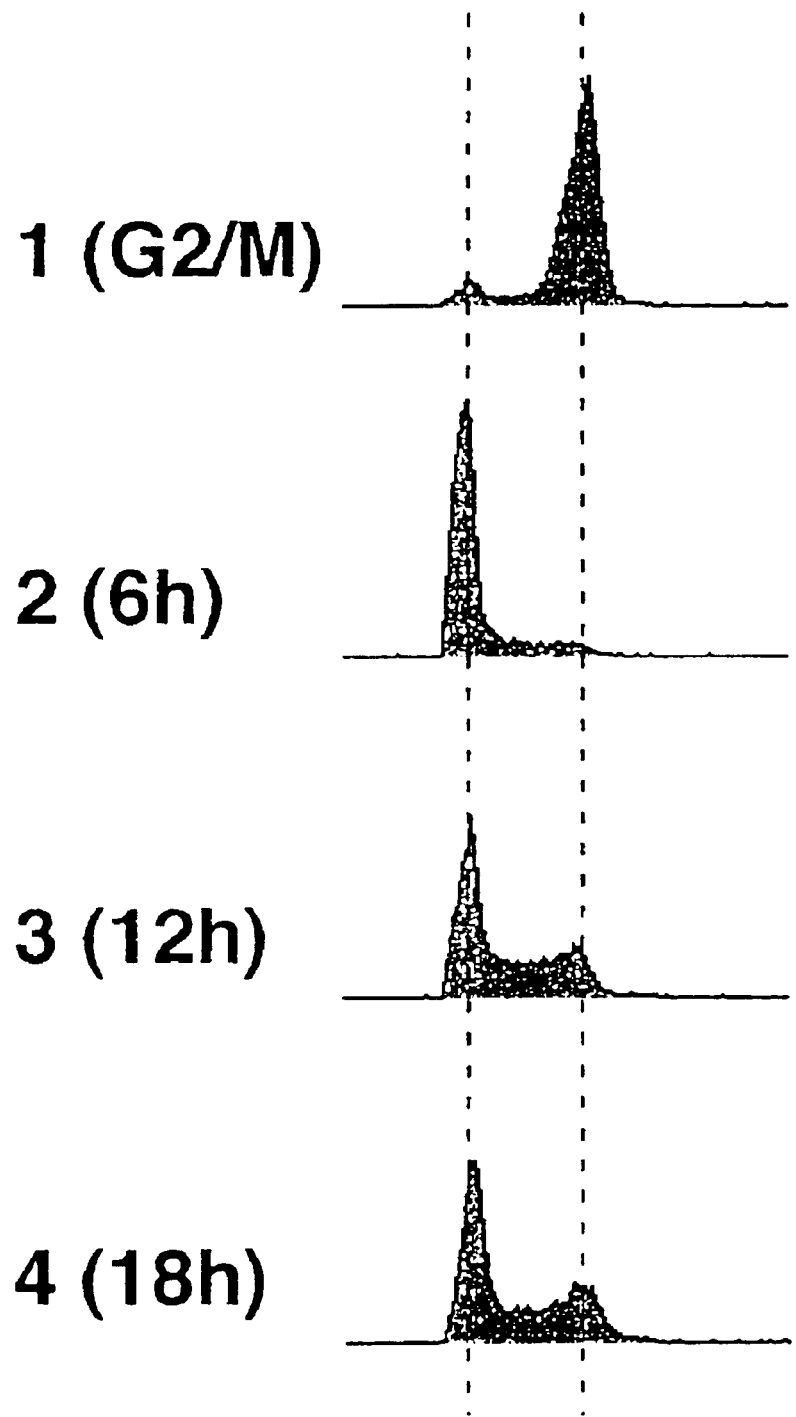

FIG. 15 shows the result of FACS analysis for DNA content in which HeLa cells were stopped at latter G2 phase using nocodazole and then the cell cycle was synchronously shifted.

Figure 16:
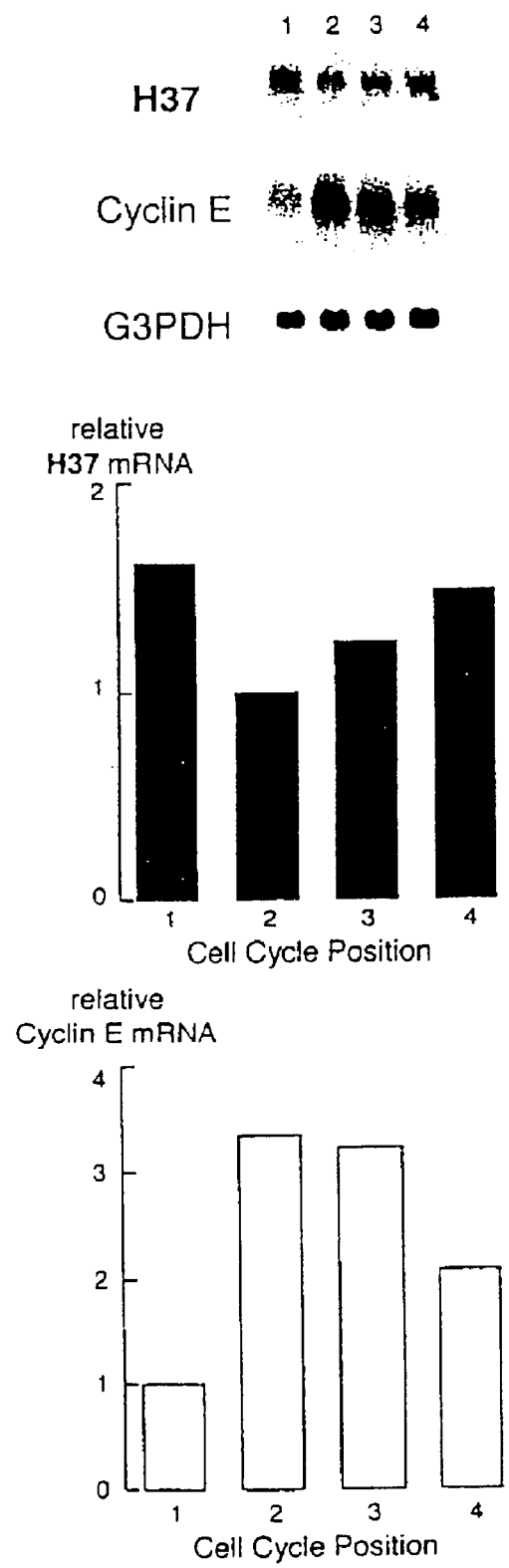

FIG. 16 shows the result northern analysis for expression of H37 and cyclin E in each cell cycle of FIG. 14 (upper), and also shows the graphs showing the relative expression amounts of each mRNA (middle and lower).

FIG. 17 shows H37 localization in cells measured by indirect immunofluorescent technique. The antibodies used are anti-H37C (A), anti-H37N (C) and a control antibody (E) while B, D and F were pictures stained with DAPI.

Figure 18:
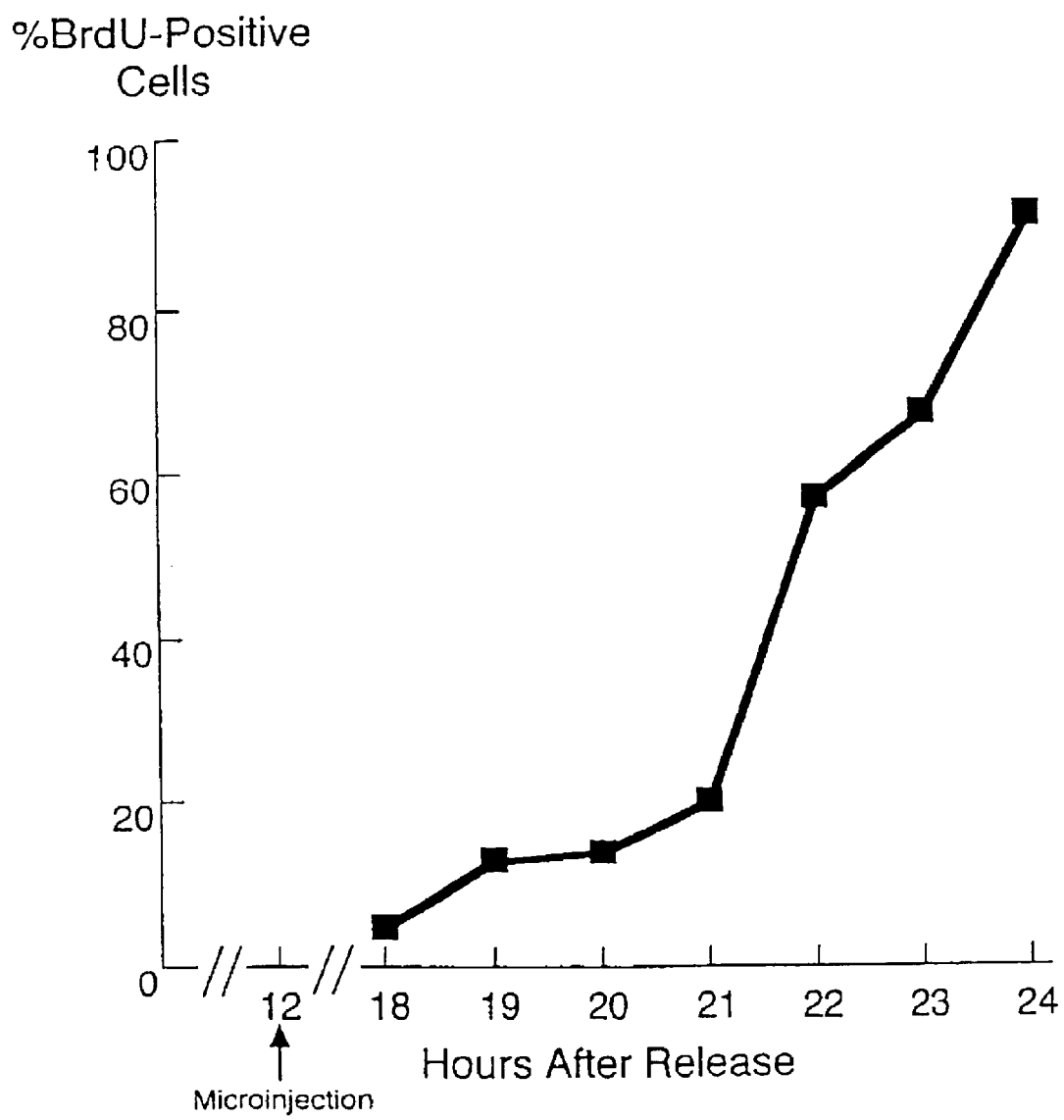

FIG. 18 shows kinetics of induction of DNA replication after serum stimulation of KD cells as measured by BrdU incorporation.

Figure 19:
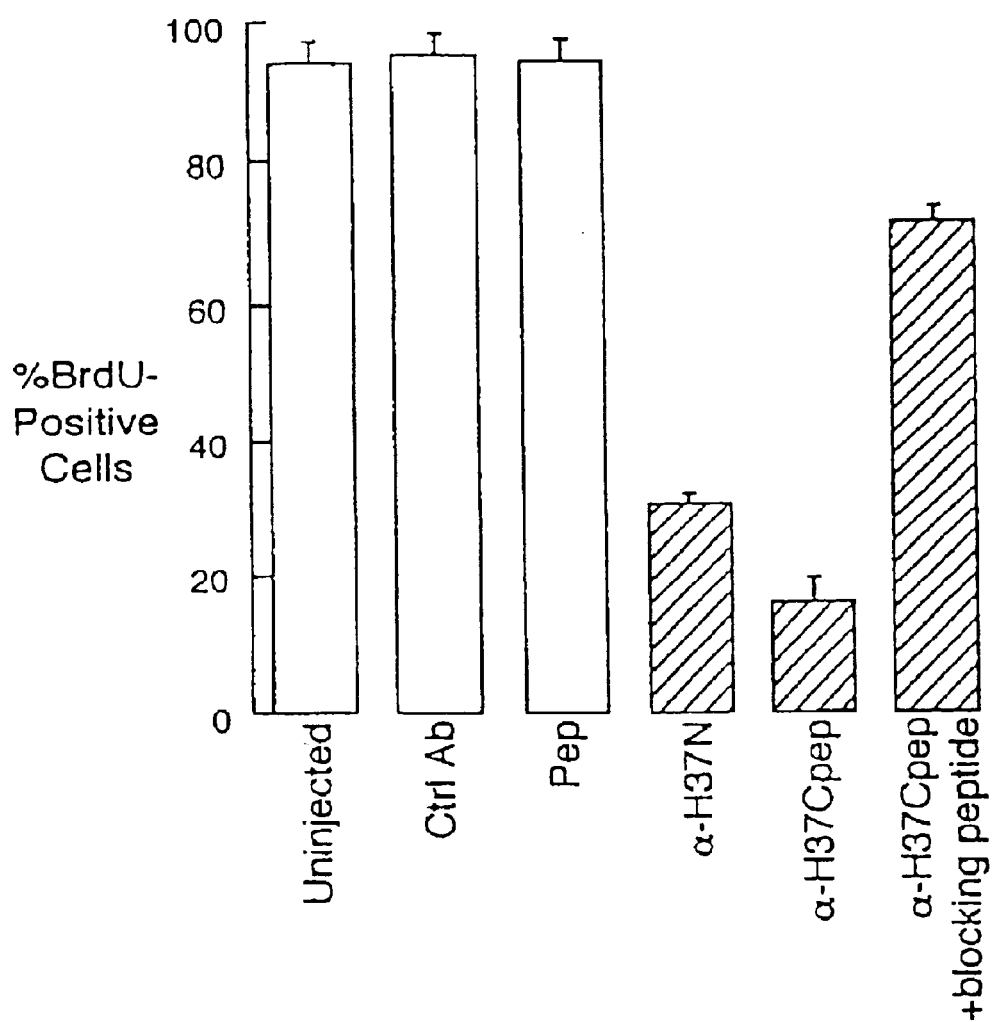

FIG. 19 shows the results in which KD cells, synchronized by serum starvation, were microinjected with various antibodies at 12 hours after serum stimulation, and then the rate of the cells incorporating the BrdU after 16 hours was measured. The numbers show the rate of the cells which are conducting the DNA synthesis.

Figure 20:
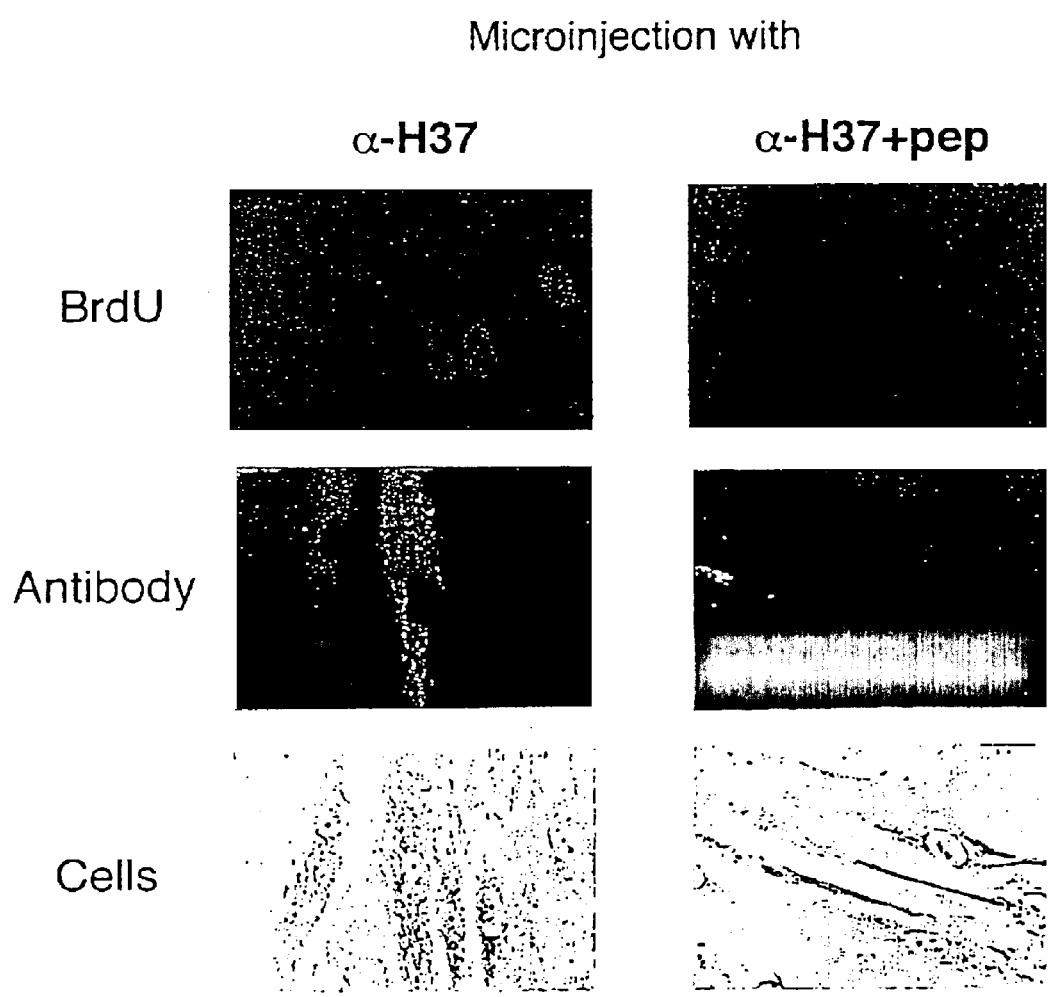

FIG. 20 is microscopic picture of examples of cells into which a mixture of anti-H37Cpep antibody and antigen peptide was microinjected. The pictures show the incorporated BrdU (upper), injected antibody (middle) and cells (lower).

DESCRIPTION OF THE PREFERRED EMBODIMENTS

The human H37 protein of this invention has the amino acid sequence of SEQ ID NO: 1 and is a protein molecule encoded in the sequence region from 518th to 2541st of cDNA whose base sequence is shown in SEQ ID NO: 3. The H37 protein of this invention also has the amino acid sequence of SEQ ID NO: 2 and is a protein encoded in the sequence region from 518th to 1222nd of cDNA whose base sequence is shown in SEQ ID NO: 4. SEQ ID NO: 3 and NO: 4 are cDNAs derived from mRNA transcribed from the same genomic gene but the cDNA of SEQ ID NO: 4 is in a different splicing form from SEQ ID NO: 3, and there is a deletion from 1199th to 1259th of SEQ ID NO: 3.

Those H37 proteins can be prepared by known methods such as isolation from human organs and cell lines, chemical synthesis of peptide based upon the amino add sequence provided by this invention, and a recombinant DNA technique using cDNA fragments provided by this invention. For example, in case the H37 protein is prepared by means of a recombinant DNA technique, RNA is prepared from a vector having the cDNA fragment of this invention by an in vitro transcription and then an in vitro translation is carried out using the above as a template whereby an expression in vitro is possible. In addition, when the translational region is recombined to a suitable vector by a known method, it is possible to express the H37 protein encoded in cDNA in a large quantity in *Escherichia coli, Bacillus subtilis*, yeast, insect cells, animal cells, etc.

When the human H37 protein of this invention is expressed in a microorganism such as *E. coli*, the translational region of cDNA of this invention is inserted into an expression vector having, for example, promoter, ribosome binding site, cDNA cloning site, terminator, origin replicable in microorganism, etc. whereupon a recombinant expression vector is prepared, then host cell is transformed using the said expression vector and the resulting transformant is incubated whereupon H37 protein encoded in cDNA can be produced in a microorganism in a large quantity. Alternatively, it can be expressed as a fusion protein with other protein. The resulting fusion protein is cleaved by an appropriate protease whereupon only the protein portion encoded in cDNA can be obtained.

When the human H37 protein of this invention is expressed in animal cells, the translational region of cDNA of this invention is recombined with expression vector for animal cells having, for example, promoter, poly(A) addition site, and splicing site, and then introduced into the animal cells whereupon the H37 protein of this invention can be expressed in animal cells.

The human H37 protein obtained by the method as mentioned above can be used as an antigen for the preparation of antibody for suppressing the proliferation of cells through inhibition of the kinase activity of huCdc7.

In addition, as will be confirmed by the Examples later, the human H37 protein of this invention has almost no similarity in terms of structure to cyclins which have been elucidated up to now, but it may be regarded as a cyclin-like associating factor for huCdc7 kinase in such respects that its expression is regulated by a cell cycle and that, as a result of binding to an huCdc7 catalytic subunit, its kinase activity can be activated. Accordingly, since the H37 protein is believed to be a very important target factor in a signal transduction pathway for the cell proliferation induced by a growth factor, elucidation of how the expression of the H37 protein or activity thereof is regulated by the signal of cell cycle in G1/S phases is expected to provide a big and novel finding for clarifying the molecular mechanism of cell cycle control of cell replication in animal cells.

The human H37 protein of the invention contains peptide fragments (five or more amino acid residues) containing any partial amino acid sequence of SEQ ID NO: 1 or NO: 2. Such peptide fragments can be also used as an antigen for the preparation of antibody.

The gene of the invention is a human gene encoding the above-mentioned human H37 protein and can be isolated from known genomic libraries using, for example, the cDNA of this invention or a partial sequence thereof as a probe.

The cDNA of the invention is characterized in having a base sequence of SEQ ID NO: 3 or NO: 4, and can be cloned, for example, from cDNA libraries derived from human cells. cDNA is synthesized using poly(A)$^+$ RNA extracted from human cells as a template. The human cells may be either those excised from human body by a surgical operation or cell lines. The cDNA can be prepared by known methods such as Okayama-Berg method (Okayama, H and Berg, P., Mol. Cell. Biol., 2:161–170, 1982), Gubler-Hoffmann method (Gubler, U. and Hoffman, J. Gene, 25:263–269, 1983) and Capping method (Kato, S. et al., Gene, 150:243–250,1994).

The human H37 protein of the invention is expressed in any tissue except brain and kidney and, therefore, when the human cDNA library prepared from human cells is screened using an oligonucleotide probe synthesized based on the base sequence of cDNA in SEQ ID NO: 3 or NO: 4, it is possible to easily prepare the clone of the invention. It is also possible that the desired cDNA is synthesized by a polymerase chain reaction (PCR) using such an oligonucleotide as a primer.

In general, polymorphism due to the difference among individuals is frequently noted in human gene. Accordingly, cDNA of SEQ ID NO: 3 or NO: 4 where one or more nucleotide(s) is/are added thereto and/or deleted therefrom and/or other nucleotide(s) is/are substituted therefor is also covered by the invention.

Similarly, the protein where one or more nucleotide(s) is/are added thereto and/or deleted therefrom and/or other nucleotide(s) is/are substituted therefor as a result of those modifications is also covered by the invention so far as it has an activity of the protein having an amino acid sequence of SEQ ID NO: 1 or NO: 2. Further, variant protein where one or more nucleotide(s) is/are added thereto and/or deleted therefrom and/or other nucleotide(s) is/are substituted by an artificial means is covered by this invention as well.

The DNA fragment of the invention covers a cDNA fragment (10 bp or more) containing any partial base sequence of SEQ ID NO: 3 or NO: 4, or a cDNA fragment comprising an antisense strand thereof.

Antibody against human H37 protein of the invention can be prepared as a polyclonal antibody or a monoclonal antibody by a known method using protein per se or a partial peptide thereof.

A method for promoting the cell proliferation according to the invention is carried out by such a manner that a recombinant DNA comprising the cDNA having a base sequence of SEQ ID NO: 3 or NO: 4, or comprising a partial sequence thereof (such as a DNA fragment encoding 419 amino acid sequence region at the C terminal as shown in Example 3) and an expression-regulatory sequence (promoter and/or enhancer sequence for animal cells) is introduced into animal cells whereby the H37 protein having an amino sequence of SEQ D NO: 1 or NO: 2 is excessively expressed in cell nuclei. Introduction of the recombinant DNA into cells can be carried out by a known method such as a calcium phosphate method, a method where ribosome and erythrocyte ghost are used, an electoporation method, a method where retrovirus or adenovirus is used as a vector and a microinjection method using a glass pipette. Promotion of cell proliferation as such is useful, for example, in a large-scale preparation of the stem cell that is useful for the therapy of human diseases. Stem cells can be differentiated into other kinds of cells such as blood stem cell and nerve stem cell, and are able to produce a large number of cells of different cell type that constitute the human body. Therefore, transplantation of stem cell in the diseases such as leukemia is a very important therapeutic means. However, since no liquid factor for self-proliferation of human stem cells without differentiation has been identified yet, the preparation of stem cells in an amount sufficient for the therapy has not been easy. According to the method of this invention, it could be possible that, as a result of manipulating the proliferation program in stem cells, the stem cells can be unlimitedly self-replicated and self-proliferated in vitro. In addition, such a promotion of cell proliferation in vitro could be also useful for the preparation of a large quantity of cells for introduction of gene for genetic therapy by ex vivo means.

The method for the suppression of cell proliferation according to the invention is carried out by injecting the above-mentioned antibody into cells. Alternatively, it may be carried out by inhibiting the expression of the cell-intrinsic H37 protein gene as well An example thereof is a method where DNA encoding the ribozyme sequence or the antisense sequence to the transcript of the gene is introduced into the cells. Suppression of the cell proliferation as such is expected to provide a novel means for suppressing an excessive proliferation of cancer cells for example.

EXAMPLES

The invention will now be further illustrated by way of the following examples although the invention is not limited to those examples.

Example 1

H37 cDNA labeled with a Flag tag was ligated to the down stream of an SRalpha promoter and introduced into IL-3 (interleukin 3)-dependent proB cell, Ba/F3, to give a stable transformant cell line constitutively expressing the Flag-tagged H37 protein. In this cell line, rate of the cell at the late S phase or G2 phase where DNA synthesis was almost finishing or was finished in the population of the proliferating cells increased as compared with the control parental cell line. On the other hand, the parental cells stopped its proliferation by removal of IL-3 and came into G0 phase but, in the stable transformant cell line, rate of the cells existing in S phase significantly increased even after the removal of IL-3. This result shows that the constitutive production of the H37 protein promotes the shift from G0/G1 phase to S phase, or the progress of S phase itself It also suggests that the progress of cell cycle can be operated by an artificial expression of the H37 protein or a derivative thereof.

Example 2 cDNA library of HeLa cell was prepared using a pGAD-GH vector and each vector was introduced into yeast strain CG1945 that has a recombinant plasmid with huCdc7 fused to DNA-binding domain of Ga14. As a result of a screening of about $3 \times 10^5$ cells of transformed yeast, five clones where β-galactosidase was positive were obtained. DNA base sequence of the insert was determined and the database was searched whereupon all of them were novel cDNA. Among them, three clones were same having a base sequence of SEQ ID NO: 1. This cDNA was named H37. Other two were single clones and were named H1 and H18, respectively.

Figure 1:
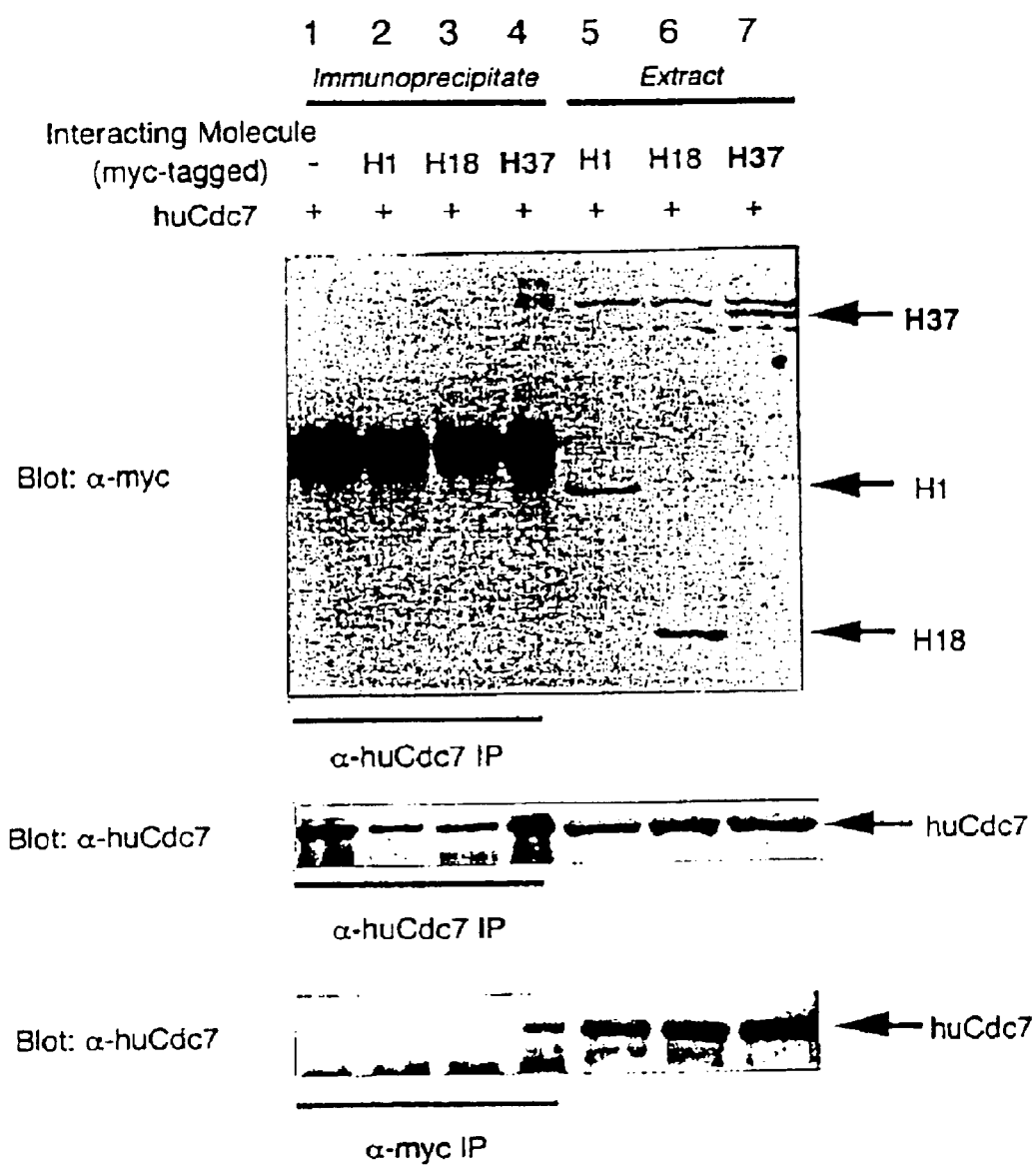
FIG. 1 is the result of a western blotting measuring the coimmunoprecipitation of H37 with huCdc7 expressed in mammalian cells. Lanes 1—4, immunoprecipitates, lanes 5—7, whole cell extract. Upper and middle panels, immunoprecipitated with anti-huCdc7 antibody No. 1; lower panel, immunoprecipitated with anti-myc antibody. Extracts were prepared from Cos7 cells transfected with huCdc7 in combination with H1 (lanes 2 and 5), H18 (lanes 3 and 6), H37 (lanes 4 and 7) or huCdc7 alone (lane 1). Western blotting was conducted with anti-myc antibody (upper panel) or an anti-huCdc7 antibody No. 1 (middle and lower panel).

The interaction of huCdc7 with protein encoded in those positive clones was further investigated using a production increase system in animal cells. Thus, each expression plasmid of H1, H18 and H37 tagged with myc epitope was transfected to animal cell Cos7 together with a full-length huCdc7 expression plasmid. The result is as shown in FIG. 1. Although the H37 protein was coimmunoprecipitated with an antibody against huCdc7, H1 and H18 proteins were not coprecipitated (cf. lanes 2–4 of the upper panel, FIG. 1). On the contrary, huCdc7 was coimmunoprecipitated by using anti-myc antibody alone in the case of the cells where myc-tagged H37 is co-expressed (cf. lane 4 of the lower lane, FIG. 1). From those results, it has been confirmed that only H37 cDNA encodes a protein efficiently interacting with huCdc7.

Figure 2:
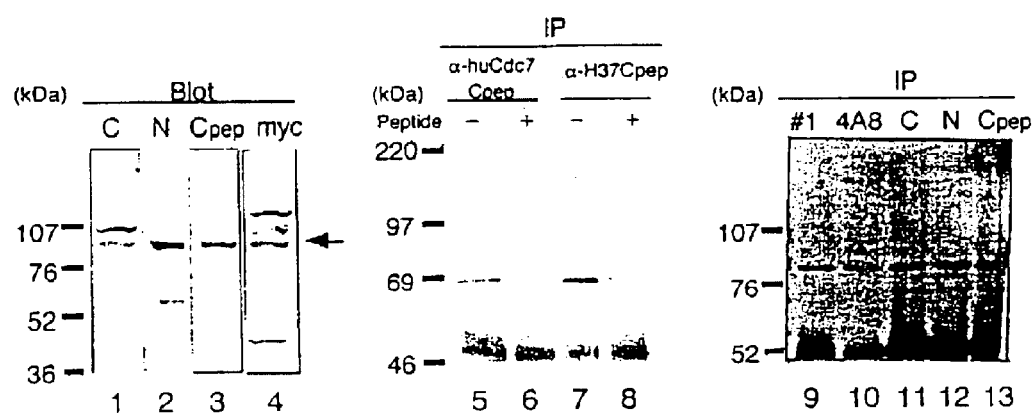
FIG. 2 is a result of the western blotting measuring antibodies against H37 protein and association of huCdc7 and H37 in vivo. Nuclear extracts prepared from Cos7 cells transfected with myc-tagged H37 cDNA were blotted with anti-H37C (lane 1), anti-H37N (lane 2), anti-H37Cpep (lane 3) or anti-myc (lane 4) antibody. The arrow indicates the myc-tagged H37 protein, which carries 63 amino acids derived from 5' non-coding region in addition to the myc-tag. Immunoprecipitations from CEM extracts using either anti-huCdc7Cpep (lanes 5 and 6) or anti-H37Cpep (lanes 7 and 8) were separated on gel electrophoresis and blotted with huCdc7 monoclonal antibody (4A8). The symbols − and + indicates absence and presence, respectively, of each antigen peptide during immunoprecipitation. Lanes 9–13; immunoprecipitates, prepared from nuclear extracts of HeLa cells by anti-huCdc7 No. 1 (lane 9), anti-huCdc7 monoclonal antibody 4A8 (lane 10), anti-H37C (lane 11), anti-H37N (lane 12) or anti-H37Cpep (lane 13), were blotted with anti-H37Cpep.

Then, in order to investigate the intrinsic H37 protein, each antibody against N- or C-terminal regions of H37 (anti-H37N antibody or anti-H37C antibody) was prepared. Further, antibody against C-terminal oligopeptide of H37 (anti-H37Cpep antibody) and antibody against C-terminal oligopeptide of huCdc7 (anti-huCdc7Cpep antibody) were also prepared. After that, association of each antibody with intrinsic huCdc7 and H37 in cells was measured. The result is as shown in FIG. 2. Thus, all of the antibodies to H37 specifically react with the myc-tagged H37 protein of 90 kDa expressed in Cos7 cells (cf. lanes 1–4, FIG. 2). Complex prepared from human CEM cells was able to be coprecipitated using an affinity-purified anti-peptide antibody. It was confirmed by an immunoblotting using anti-huCdc7Cpep antibody that all of huCdc7 and H37 immunoprecipitates contained huCdc7 (lanes 5 and 7, FIG. 2). This interaction of H37 with huCdc7 completely disappeared when antibody and peptide used as antigen for preparing the antibody were subjected to a pre-incubation in advance (cf. lane 8, FIG. 2). In extracts of HeLa cells, both anti-Cdc7 antibody and anti-H37 antibody were able to coprecipitate one polypeptide of 80 kDa that specifically reacted with anti-H37 antibody lanes 9–13, FIG. 2).

From the above result, it was found that intrinsic huCdc7 and H37 protein were present in cells as a complex.

Example 3

Figure 3:
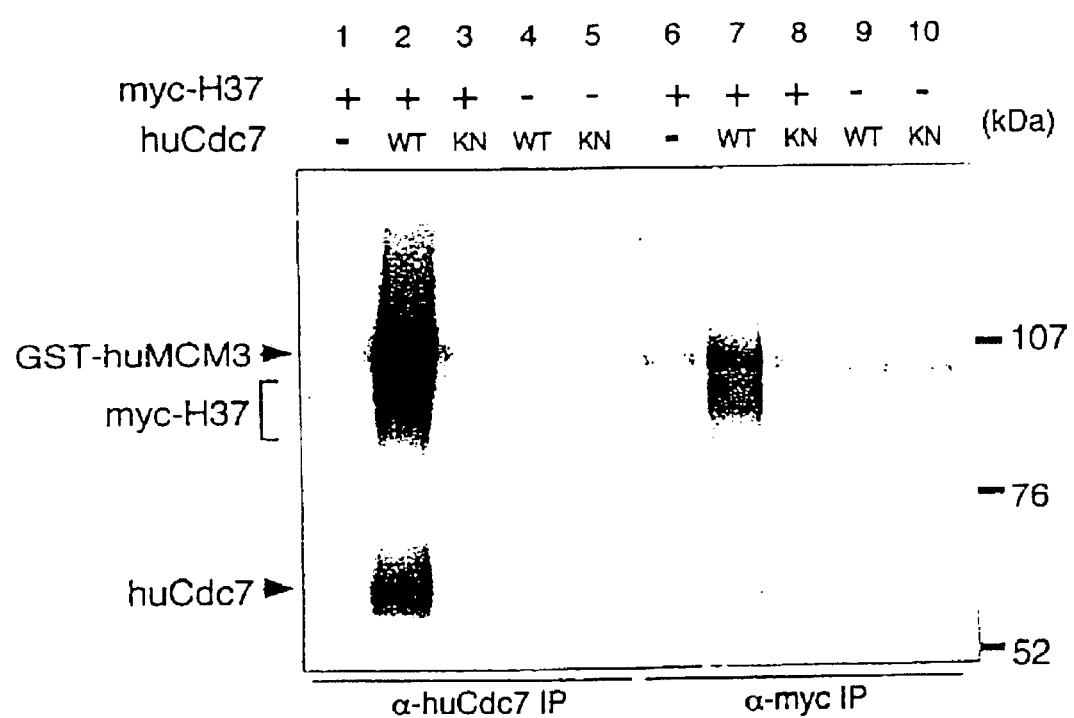
FIG. 3 shows the result of immunoprecipitation by the use of anti-huCdc7 antibody No. 1 (lanes 1–5) or anti-myc antibody (lanes 6–10) from the extract of Cos7 cells transfected with myc-tagged H37 alone (lanes 1 and 6), or together with wild-type huCdc7 (lanes 2 and 7), or kinase negative huCdc7 (lanes 3 and 8). Wild-type huCdc7 alone (lanes 4 and 9) and kinase negative huCdc7 alone (lanes 5 and 10) were included as control.

In order to investigate whether H37 protein has an ability of activating huCdc7, huCdc7/H37 complex prepared by expression of myc-tagged H37 and wild-type or kinase negative huCdc7 in Cos cells was immunoprecipitated by anti-huCdc7 antibody or anti-myc antibody and then a kinase reaction in vitro was measured using GST-MCM3 fusion protein as a substrate. The result is as shown in FIG. 3 and in FIG. 4. In the presence of wild-type huCdc7, phosphorylation in a good efficiency was observed for the MCM3 protein in both immunoprecipitate of anti-huCdc7 antibody and immunoprecipitate of anti-myc antibody (cf. lanes 2 and 7, FIG. 3). Further, two more phosphorylated proteins were observed and they were identified as transfected huCdc7 and myc-tagged H37 (data not shown). Since the phosphorylation as such was not detected at all in kinase negative huCdc7, it was confirmed that kinase activity of huCdc7 acted in the phosphorylation. However, kinase negative huCdc7 was also able to form a complex with H37 protein (cf. lanes 3 and 8, FIG. 3; lanes 2 and 4, FIG. 4). In addition, the mobility of H37 protein on gel electrophoresis was slow when a wild-type huCdc7 was compressed and detected as plural bands while such a shift was not observed i kinase negative huCdc7 (cf. lanes 1 and 3, FIG. 4). The band where the mobility was slow disappeared by a treatment with phosphatase and, therefore, it was confirmed to be a perphosphorylated H37 protein (data not shown). In addition, when huCdc7 and H37 protein were co-expressed in insect cells, it was possible to reconstitute a very strong kinase activity which was able to efficiently phosphorylate MCM2 and MCM3 proteins (data now shown).

The above result shows that H37 protein activates huCdc7 kinase and further that H37 protein itself is phosphorylated by huCdc7.

Further, under those experimental conditions, intrinsic H37 protein level was too low and in the case where only huCdc7 catalytic subunit was expressed and, therefore, the kinase activity was little (cf. lanes 4 and 9, FIG. 3). From those facts, it was confirmed that H37 protein encoded regulatory cell unit of huCdc7 and specifically activated its kinase activity.

Example 4

An amino acid sequence of the H37 protein (SEQ ID NO: 1) was analyzed. The result was that, as shown in FIG. 5 and FIG. 6, an amino acid sequence region having a homology of 33% with budding yeast Dbf4 was found. This conserved domain (H37 motif C) was also present in the gene similar to H37 identified in mouse, fruit fly and fission yeast (cf. FIG. 6). Further, another amino acid sequence of H37 (H37 motif N) was conserved in the EH37-related gene in mouse, fruit fly and fission yeast. However, the H37 motif N was conserved in a somewhat modified form on the Dbf4 protein of a budding yeast (cf. FIG. 6; data partial not shown).

In order to determine the region on H37 protein essential for binding with huCdc7, a series of deletion derivatives of H37 at N- and C-terminals as shown in FIG. 7 was prepared, each of them was expressed in yeast as a fusion protein with Gal4 activated domain and an interaction of each deletion derivative with huCdc7 was investigated by means of a two-hybrid assay. The result is as shown in FIG. 8. As a result of deletion at N-terminal, even a deletion of 255 amino acids at N-terminal did not affect the interaction with huCdc7 (ΔN2). However, when 50 amino acids at N-terminal were further deleted whereupon the H37 motif C was deleted, an interaction with huCdc7 was completely lost (ΔN3).

On the other hand, with regard to deletion from C-terminal, when only 20 amino acids were deleted, the binding ability with huCdc7 decreased to an extent of about 60% (ΔC). In addition, when 243 or 369 amino acids were deleted from the C-terminal (ΔP2 and ΔB), the interaction lowered to an extent of about 10% of the full-length done. ΔP1 containing only 235 amino acids of N-terminal did not interact with huCdc7. However, 50 amino acids that were commonly present in ΔB and ΔN2 were not sufficient for an efficient interaction with huCdc7 (data not shown).

A part of the above-mentioned H37 deletion derivatives was co expressed in COS7 cells together with huCdc7 and it was confirmed by immunoprecipitation method whether it formed a complex with huCdc7 protein. The result was that, like in the result of a two-hybrid assay, it was confirmed that only H37 deletion derivatives of deltaB and deltaN2 formed a complex with huCdc7 (cf. FIG. 9).

The above result shows that H37 motif-C is essential for an interaction of H37 protein with huCdc7 catalytic subunit but shows that H37 motif C alone is insufficient. In the budding yeast, it was reported already that the region containing H37 motif C was sufficient for binding with Cdc7 (Mol. Cell. Biol. 15:6775–6782, 1996). When an in vitro kinase reaction was carried out using those deletion derivatives, it was found that, although the extent was weak, only 419 amino acids at the C-terminal containing Dbf4 motif-C was sufficient for activation of phosphorylating ability of huCdc7 (data not shown).

Example 5

Expression patterns of H37 mRNA in various human tissues and cancer cells were investigated by northern blotting. The result is as shown in FIGS. 10(a) and (b). By an H37 cDNA-specific probe, a transcribed product of 2.5 kb was detected in all tissues except brain and kidney and also in all cancer cells. That was contrary to the fact that, in brain and kidney, huCdc7 mRNA was relatively highly expressed (EMBO J. 16:4340–4351, 1997). Among the tissues tested, expression of H37 mRNA was highest in testicles and then in thymus, and it was reported by the inventors already that both of them were the tissues where the expression of huCdc7 catalytic subunit was particularly high as well (EMBO J. 16:4340–4351, 1997). In the testicles, two different RMA bands of 6 kb and 4 kb were also detected (cf. FIG. 10(a)) although it was ambiguous what the real substances therefor were. It was also confirmed that H37 mRNA was expressed in a very high level in nearly all cancer cells except lung cancer cell A549 (cf. FIG. 10(b)). That shows an important role of H37 protein in the cells having an active proliferating ability.

Example 6

In order to investigate whether expression of H37 was regulated by cell cycle, human normal fibroblast cell WI38 was synchronized with G0 phase by means of serum starvation (cf. FIG. 11), total RNA was prepared at various periods after addition of serum and the level of H37 mRNA was investigated by northern blotting. The result is as shown in FIG. 12. H37 mRNA level was low in the cell at the resting stage and, as the cells came near the boundary of G1 and S, it gradually increased and, after 20 hours from the serum addition, it became maximum. The expression pattern shown in FIG. 12 was similar to that of transcribed product of huCdc6 that is know to be induced by growth stimulation (Mol. Cell. Biol. 15:4215–4224, 1995; Proc. Natl. Acad. Sci. USA 94:142–147, 1997).

Further, in order to investigate the changes in expression of H37 in cell cycle, human CEM cells were fractionated by means of elutriation method (cf. FIG. 13) and then a northern blotting was carried out (cf. FIG. 14). It was shown by the result thereof that H37 mRNA was low at G1 phase, increased from the late G1 phase to S phase, highly maintained during S phase and somewhat decreased in G2 phase although it was still kept high. In an experiment where HeLa cells were stopped at G2 phase by nocodazole and the cell cycle was synchronously shifted (cf. FIG. 15), it was also found that H37 mRNA decreased together with shift from G2 to G1 and increased again at shift to S phase (cf. FIG. 16). Similarly, expression of Cdc6 rose together with shift from G1 phase to S phase but there was a difference from H37 in that, as S phase proceeded, it decreased and, at G2 phase it was suppressed to low. The result shows that the expression of H37 mRNA changes even in the proliferating cell cycle, becomes maximum at S phase where it functions and is kept high throughout S phase.

After that, in order to investigate the changes in H37 protein and huCdc7 kinase activity depending upon H37 in cell cycle, amount of H37 protein in K562 cells synchronized with nocodazole was analyzed by western analysis while Cdc7 kinase activity was analyzed by phosphorylation reaction of GST-huMCM2 protein using anti-huCdc7 immunoprecipitate in the same manner as in FIG. 15. Although H37 protein was not detected from G1/M boundary to G1 phase, it started to be detected at the G1/S boundary and detected throughout S phase. This was in contrast to the fact that cyclin E protein is detected already in G1 phase and, as S phase proceeds, the amount suddenly decreases. On the other hand, huCdc kinase activity was also detected in S phase only corresponding to the level of H37 protein.

Further, H37 protein was detected as plural phosphorylated bands in S phase and was thought to be phosphorylated by huCdc7 that was probably associated. On the contrary, level of huCdc7 protein was almost constant throughout cell cycle. This result proves that the level of huCdc7 protein varies in cell cycle and is kept high in S phase whereby huCdc7 kinase activity is also kept high in S phase.

In order to further investigate the expression of H37, intracellular localization of H37 protein in animal cells was measured. The result of indirect fluorescent antibody method using two kinds of H37-specific antibodies was that, in both HeLa and WI38 cells, intrinsic H37 protein was observed as very clear various spots in the nuclei (cf. FIG. 17).

When those results and the intranuclear localization of huCdc7 catalytic subunit already reported by the inventors (EMBO J. 16:4340–4351, 1997) were taken into consideration, it was confirmed that huCdc7/H37 complex was a kinase localized in the nuclei and that its regulatory subunit H37 was expressed depending upon the stage of cell cycle.

Example 7

Function of the intrinsic H37 protein in the shift from G1 to S in cell cycle was investigated by antibody microinjection method. Antibody against N-terminal 305 amino acids of H37 protein (anti-H37N antibody) and antibody against C-terminal oligopeptide (anti-H37Cpep antibody) were treated by affinity purification and those antibodies were microinjected into normal fibroblast cells (KD cells) derived from human lip. KD cells were previously arrested at G0 phase by means of serum starvation and then synchronously proceeded in cell cycle by re-addition of serum. Numbers of the BrdU-positive cells, which BrdU is a nucleotide derivative and is incorporated into the cells, were measured whereby it was investigated how much fractions of cells at S phase were present after various stages after addition of serum. The result is as shown in FIG. 18. It was confirmed that the cells started DNA synthesis after about 18 hours from serum addition and that, after 24 hours, almost 90% of the cells were in S phase.

Accordingly, in this Example, antibody was microinjected at the period of after 12 hours after the addition of serum where the cells were still in G1 phase and, at 26 hours when cells would be of in S phase, the cells were fixed and the BrdU-positive cells were measured. The result is as shown in FIG. 19. Although 70% of the cells into which anti-H37N antibody was microinjected did not shift into S phase, there was nearly no effect by the control antibody. Even by the microinjection of the anti-H37Cpep antibody, an effect of inhibiting the shift to S phase which was same as or even more than the anti-H37N antibody was observed. In addition, when anti-H37Cpep antibody and a peptide which was an antigen for the preparation of anti-H37Cpep antibody were simultaneously microinjected into the cells, 70% or more of the cells were shifted to S phase.

FIG. 20 is a staining example of BrdU and microinjected antibody. The antibody was microinjected at the stage when the cells were from the mid to late S phase and, during that period, expression of H37 protein is believed to be low. The microinjected antibody efficiently bound to the freshly synthesized H37 protein and, as a result, it is speculated to inhibit the transfer of H37 protein into nucleus. Those results strongly suggest the function of H37, i.e. the function of huCdc7/H37 complex is required for the progression of S phase of the animal cells.

As fully illustrated hereinabove, the present invention provided human H37 protein, a regulatory subunit for Cdc7 that regulate replication of human cells, human gene encoding this protein as well as cDNA thereof, an antibody against H37 protein, and a method for controlling the proliferation of human cells using those genetic engineering materials and antibody. As a result, it provides potentially novel means for preparation of the necessary amount of stem cells or the like to be used for the therapy of various human diseases or for the suppression of proliferation of cancer cells.

What is claimed is:

1. An isolated human protein comprising the amino acid sequence of SEQ ID NO: 1.
2. An isolated human protein comprising the amino acid sequence of SEQ ID NO: 2.
3. An isolated polypeptide consisting of the amino acid sequence of SEQ ID NO: 1.
4. An isolated polypeptide consisting of the amino acid sequence of SEQ ID NO: 2.
5. An isolated cDNA encoding the human protein of claim 1 or 2.
6. The cDNA of claim 5, which comprises the nucleotide sequence of SEQ ID NO: 3.
7. The cDNA of claim 5, which comprises the nucleotide sequence of SEQ ID NO: 4.
8. A recombinant vector comprising the cDNA of claim 6.
9. A recombinant vector comprising the cDNA of claim 7.
10. An isolated polynucleotide encoding the polypeptide of claim 3 or 4.
11. The polynucleotide of claim 10, which comprises the nucleotide sequence of SEQ ID NO: 3.
12. The polynucleotide of claim 10, which comprises the nucleotide sequence of SEQ ID NO: 4.
13. A recombinant vector comprising the polynucleotide of claim 11.
14. A recombinant vector comprising the polynucleotide of claim 12.
15. An isolated monoclonal antibody which binds specifically against the human protein of claim 1.
16. An isolated monoclonal antibody which binds specifically against the human protein of claim 2.
17. An isolated monoclonal antibody which binds specifically against the polypeptide of claim 3.
18. An isolated monoclonal antibody which binds specifically against the polypeptide of claim 4.
19. A method for promoting the proliferation of cells in vitro, which comprises introducing the cDNA of claim 6 together with an expression regulatory sequence into the cells.
20. A method for promoting the proliferation of cells in vitro, which comprises introducing the cDNA of claim 7 together with an expression regulatory sequence into the cells.
21. A method for promoting the proliferation of cells in vitro, which comprises introducing the polynucleotide of claim 11 together with an expression regulatory sequence into the cells.
22. A method for promoting the proliferation of cells in vitro, which comprises introducing the polynucleotide of claim 12 together with an expression regulatory sequence into the cells.
23. A method for suppressing the proliferation of cells in vitro which comprises introducing the antibody of claim 15 into the cells.
24. A method for suppressing the proliferation of cells in vitro, which comprises introducing the antibody of claim 16 into the cells.
25. A method for suppressing the proliferation of cells in vitro, which comprises introducing the antibody of claim 17 into the cells.
26. A method for suppressing the proliferation of cells in vitro, which comprises introducing the antibody of claim 18 into the cells.

* * * * *

UNITED STATES PATENT AND TRADEMARK OFFICE
CERTIFICATE OF CORRECTION

PATENT NO.        : 6,897,054 B1
APPLICATION NO. : 09/830647
DATED             : May 24, 2005
INVENTOR(S)       : Kenichi Arai et al.

It is certified that error appears in the above-identified patent and that said Letters Patent is hereby corrected as shown below:

Page 1, Section (54), please change "CDNA" to -- cDNA --.

Page 1, Section (73), after "(JP)" please insert the following additional Assignee information: -- Kenichi Arai, Tokyo (JP) and Hisao Masai, Tokyo (JP) --.

Signed and Sealed this

Thirteenth Day of February, 2007

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 674
<212> TYPE: PRT
<213> ORGANISM: Homo sapiens

<400> SEQUENCE: 1

Met Asn Ser Gly Ala Met Arg Ile His Ser Lys Gly His Phe Gln Gly
 1               5                  10                  15

Gly Ile Gln Val Lys Asn Glu Lys Asn Arg Pro Ser Leu Lys Ser Leu
            20                  25                  30

Lys Thr Asp Asn Arg Pro Glu Lys Ser Lys Cys Lys Pro Leu Trp Gly
        35                  40                  45

Lys Val Phe Tyr Leu Asp Leu Pro Ser Val Thr Ile Ser Glu Lys Leu
    50                  55                  60

Gln Lys Asp Ile Lys Asp Leu Gly Gly Arg Val Glu Glu Phe Leu Ser
65                  70                  75                  80

Lys Asp Ile Ser Tyr Leu Ile Ser Asn Lys Lys Glu Ala Lys Phe Ala
                85                  90                  95
```

```
Gln Thr Leu Gly Arg Ile Ser Pro Val Pro Ser Pro Glu Ser Ala Tyr
            100                 105                 110
Thr Ala Glu Thr Thr Ser Pro His Pro Ser His Asp Gly Ser Ser Phe
            115                 120                 125
Lys Ser Pro Asp Thr Val Cys Leu Ser Arg Gly Lys Leu Leu Val Glu
            130                 135             140
Lys Ala Ile Lys Asp His Asp Phe Ile Pro Ser Asn Ser Ile Leu Ser
145                 150                 155                 160
Asn Ala Leu Ser Trp Gly Val Lys Ile Leu His Ile Asp Asp Ile Arg
                165                 170                 175
Tyr Tyr Ile Glu Gln Lys Lys Glu Leu Tyr Leu Lys Lys Ser
                180                 185                 190
Ser Thr Ser Val Arg Asp Gly Gly Lys Arg Val Gly Ser Gly Ala Gln
            195                 200                 205
Lys Thr Arg Thr Gly Arg Leu Lys Lys Pro Phe Val Lys Val Glu Asp
            210                 215                 220
Met Ser Gln Leu Tyr Arg Pro Phe Tyr Leu Gln Leu Thr Asn Met Pro
225                 230                 235                 240
Phe Ile Asn Tyr Ser Ile Gln Lys Pro Cys Ser Pro Phe Asp Val Asp
                245                 250                 255
Lys Pro Ser Ser Met Gln Lys Gln Thr Gln Val Lys Leu Arg Ile Gln
            260                 265                 270
Thr Asp Gly Asp Lys Tyr Gly Gly Thr Ser Ile Gln Leu Gln Leu Lys
            275                 280                 285
Glu Lys Lys Lys Gly Tyr Cys Glu Cys Leu Gln Lys Tyr Glu
290                 295                 300
Asp Leu Glu Thr His Leu Leu Ser Glu Gln His Arg Asn Phe Ala Gln
305                 310                 315                 320
Ser Asn Gln Tyr Gln Val Val Asp Asp Ile Val Ser Lys Leu Val Phe
                325                 330                 335
Asp Phe Val Glu Tyr Glu Lys Asp Thr Pro Lys Lys Arg Ile Lys
                340                 345                 350
Tyr Ser Val Gly Ser Leu Ser Pro Val Ser Ala Ser Val Leu Lys Lys
            355                 360                 365
Thr Glu Gln Lys Glu Lys Val Glu Leu Gln His Ile Ser Gln Lys Asp
            370                 375                 380
Cys Gln Glu Asp Asp Thr Thr Val Lys Glu Gln Asn Phe Leu Tyr Lys
385                 390                 395                 400
Glu Thr Gln Glu Thr Glu Lys Lys Leu Leu Phe Ile Ser Glu Pro Ile
                405                 410                 415
Pro His Pro Ser Asn Glu Leu Arg Gly Leu Asn Glu Lys Met Ser Asn
            420                 425                 430
Lys Cys Ser Met Leu Ser Thr Ala Glu Asp Ile Arg Gln Asn Phe
            435                 440                 445
Thr Gln Leu Pro Leu His Lys Asn Lys Gln Glu Cys Ile Leu Asp Ile
            450                 455                 460
Ser Glu His Thr Leu Ser Glu Asn Asp Leu Glu Glu Leu Arg Val Asp
465                 470                 475                 480
His Tyr Lys Cys Asn Ile Gln Ala Ser Val His Val Ser Asp Phe Ser
                485                 490                 495
Thr Asp Asn Ser Gly Ser Gln Pro Lys Gln Lys Ser Asp Thr Val Leu
            500                 505                 510
```

```
Phe Pro Ala Lys Asp Leu Lys Glu Lys Asp Leu His Ser Ile Phe Thr
            515                 520                 525
His Asp Ser Gly Leu Ile Thr Ile Asn Ser Ser Gln Glu His Leu Thr
            530                 535                 540
Val Gln Ala Lys Ala Pro Phe His Thr Pro Pro Glu Glu Pro Asn Glu
545                 550                 555                 560
Cys Asp Phe Lys Asn Met Asp Ser Leu Pro Ser Gly Lys Ile His Arg
                565                 570                 575
Lys Val Lys Ile Ile Leu Gly Arg Asn Arg Lys Glu Asn Leu Glu Pro
                580                 585                 590
Asn Ala Glu Phe Asp Lys Arg Thr Glu Phe Ile Thr Gln Glu Glu Asn
                595                 600                 605
Arg Ile Cys Ser Ser Pro Val Gln Ser Leu Leu Asp Leu Phe Gln Thr
            610                 615                 620
Ser Glu Glu Lys Ser Glu Phe Leu Gly Phe Thr Ser Tyr Thr Glu Lys
625                 630                 635                 640
Ser Gly Ile Cys Asn Val Leu Asp Ile Trp Glu Glu Asn Ser Asp
                645                 650                 655
Asn Leu Leu Thr Ala Phe Phe Ser Pro Ser Thr Ser Thr Phe Thr
                660                 665                 670
Gly Phe
    674
```

<210> SEQ ID NO 2
<211> LENGTH: 234
<212> TYPE: PRT
<213> ORGANISM: Homo sapiens

<400> SEQUENCE: 2

```
Met Asn Ser Gly Ala Met Arg Ile His Ser Lys Gly His Phe Gln Gly
  1               5                  10                  15
Gly Ile Gln Val Lys Asn Glu Lys Asn Arg Pro Ser Leu Lys Ser Leu
                20                  25                  30
Lys Thr Asp Asn Arg Pro Glu Lys Ser Lys Cys Lys Pro Leu Trp Gly
            35                  40                  45
Lys Val Phe Tyr Leu Asp Leu Pro Ser Val Thr Ile Ser Glu Lys Leu
 50                  55                  60
Gln Lys Asp Ile Lys Asp Leu Gly Gly Arg Val Glu Glu Phe Leu Ser
 65                  70                  75                  80
Lys Asp Ile Ser Tyr Leu Ile Ser Asn Lys Lys Glu Ala Lys Phe Ala
                85                  90                  95
Gln Thr Leu Gly Arg Ile Ser Pro Val Pro Ser Pro Glu Ser Ala Tyr
            100                 105                 110
Thr Ala Glu Thr Thr Ser Pro His Pro Ser His Asp Gly Ser Ser Phe
            115                 120                 125
Lys Ser Pro Asp Thr Val Cys Leu Ser Arg Gly Lys Leu Leu Val Glu
            130                 135                 140
Lys Ala Ile Lys Asp His Asp Phe Ile Pro Ser Asn Ser Ile Leu Ser
145                 150                 155                 160
Asn Ala Leu Ser Trp Gly Val Lys Ile Leu His Ile Asp Asp Ile Arg
                165                 170                 175
Tyr Tyr Ile Glu Gln Lys Lys Glu Leu Tyr Leu Leu Lys Lys Ser
                180                 185                 190
Ser Thr Ser Val Arg Asp Gly Gly Lys Arg Val Gly Ser Gly Ala Gln
            195                 200                 205
```

-continued

Lys Thr Arg Thr Gly Arg Leu Lys Lys Pro Phe Val Lys Val Glu Asp
    210                 215                 220

Met Ser Gln Ser Pro Ala Val His Leu Met
225                 230             234

<210> SEQ ID NO 3
<211> LENGTH: 2780
<212> TYPE: DNA
<213> ORGANISM: Homo sapiens

<400> SEQUENCE: 3

| | | | | | |
|---|---|---|---|---|---|
| aattcggcac | gagctctctg | aggctgcgcc | aagacctgaa | gcggcggacc | gagagcccgg | 60 |
| gtctgagact | gagagagcaa | cggaatggag | gcggggtaga | ggcggaaaca | caacctgcag | 120 |
| ggccagagcg | aggcgcgaga | aggacggcgg | cgtgaggggg | cggggcgcgc | agcgcgagaa | 180 |
| ggcaggcacg | aggggcgagc | gcgaggcggg | gcacggcgcg | tggcgtgaga | cggggcgggg | 240 |
| cgcgcgtatc | ggcgccgcgg | ccgcgtgacg | cgttttcaaa | tcttcaaccg | ccgcagccca | 300 |
| ctcgtttgtg | ctttgcgcct | tcctcctccg | cgccttggag | ccggatccgg | ccccggaaac | 360 |
| ccgacctgca | gacgcggtac | ctctactgcg | tagaggccgt | agctggcgga | aggagagagg | 420 |
| cggccgtcct | gtcaacaggc | cgggggaagc | cgtgctttcg | cggctgcccg | gtgcgacact | 480 |
| ttctccggac | ccagcatgta | ggtgccgggc | gactgccatg | aactccggag | ccatgaggat | 540 |
| ccacagtaaa | ggacatttcc | agggtggaat | ccaagtcaaa | aatgaaaaaa | acagaccatc | 600 |
| tctgaaatct | ctgaaaactg | ataacaggcc | agaaaaatcc | aaatgtaagc | cactttgggg | 660 |
| aaaagtattt | taccttgact | taccttctgt | caccatatct | gaaaaacttc | aaaaggacat | 720 |
| taaggatctg | ggagggcgag | ttgaagaatt | tctcagcaaa | gatatcagtt | atcttatttc | 780 |
| aaataagaag | gaagctaaat | ttgcacaaac | cttgggtcga | atttctcctg | taccaagtcc | 840 |
| agaatctgca | tatactgcag | aaaccacttc | acctcatccc | agccatgatg | gaagttcatt | 900 |
| taagtcacca | gacacagtgt | gtttaagcag | aggaaaatta | ttagttgaaa | agctatcaa | 960 |
| ggaccatgat | tttattcctt | caaatagtat | attatcaaat | gccttgtcat | ggggagtaaa | 1020 |
| aattcttcat | attgatgaca | ttagatacta | cattgaacaa | agaaaaaaag | agttgtattt | 1080 |
| actcaagaaa | tcaagtactt | cagtaagaga | tggggcaaa | agagttggta | gtggtgcaca | 1140 |
| aaaaacaaga | acaggaagac | tcaaaaagcc | ttttgtaaag | gtggaagata | tgagccaact | 1200 |
| ttataggcca | ttttatcttc | agctgaccaa | tatgcctttt | ataaattatt | ctattcagaa | 1260 |
| gccctgcagt | ccatttgatg | tagacaagcc | atctagtatg | caaaagcaaa | ctcaggttaa | 1320 |
| actaagaatc | caaacagatg | gcgataagta | tggtggaacc | tcaattcaac | tccagttgaa | 1380 |
| agagaagaag | aaaaaaggat | attgtgaatg | ttgcttgcag | aaatatgaag | atctagaaac | 1440 |
| tcaccttcta | agtgagcaac | acagaaactt | gcacagagt | aaccagtatc | aagttgttga | 1500 |
| tgatattgta | tctaagttag | ttttttgactt | tgtggaatat | gaaaaggaca | cacctaaaaa | 1560 |
| gaaaagaata | aaatacagtg | ttggatccct | ttctcctgtt | tctgcaagtg | tcctgaaaaa | 1620 |
| gactgaacaa | aaggaaaaag | tggaattgca | acatatttct | cagaaagatt | gccaggaaga | 1680 |
| tgatacaaca | gtgaaggagc | agaatttcct | gtataaagag | acccaggaaa | ctgaaaaaaa | 1740 |
| gctcctgttt | atttcagagc | ccatccccca | cccttcaaat | gaattgagag | gcttaatga | 1800 |
| gaaaatgagt | aataaatgtt | ccatgttaag | tacagctgaa | gatgacataa | gacagaattt | 1860 |
| tacacagcta | cctctacata | aaaacaaaca | ggaatgcatt | cttgacattt | ccgaacacac | 1920 |

```
attaagtgaa aatgacttag aagaactaag ggtagatcac tataaatgta acatacaggc    1980
atctgtacat gtttctgatt tcagtacaga taatagtgga tctcaaccaa aacagaagtc    2040
agatactgtg cttttccag caaaggatct caaggaaaag gaccttcatt caatatttac     2100
tcatgattct ggtctgataa caataaacag ttcacaagag cacctaactg ttcaggcaaa    2160
ggctccattc catactcctc ctgaggaacc caatgaatgt gacttcaaga atatggatag    2220
tttaccttct ggtaaaatac atcgaaaagt gaaaataata ttaggacgaa atagaaaaga    2280
aaatctggaa ccaaatgctg aatttgataa aagaactgaa tttattacac aagaagaaaa    2340
cagaatttgt agttcaccgg tacagtcttt actagacttg tttcagacta gtgaagagaa    2400
atcagaattt ttgggtttca aagctacac agaaaagagt ggtatatgca atgttttaga     2460
tatttgggaa gaggaaaatt cagataatct gttaacagcg ttttctcgt ccccttcaac     2520 ttctacattt actggctttt agaatttaaa aaatgcatac ttttcagaag tgataaggat    2580
catattcttg aaattttat aaatatgtat ggaaattctt aggatttttt taccagcttt     2640
gtttacagac ccaaatgtaa atattaaaaa taaatatttg caattttcta cagaattgaa    2700
tacctgttaa agaaaatta cagaataaac ttgtgactgg tcttgtttta cattaaaaaa     2760
aaaaaaaaaa aaaactcgag                                                2780

<210> SEQ ID NO 4
<211> LENGTH: 2719
<212> TYPE: DNA
<213> ORGANISM: Homo sapiens

<400> SEQUENCE: 4
aattcggcac gagctctctg aggctgcgcc aagacctgaa gcggcggacc gagagcccgg     60
gtctgagact gagagagcaa cggaatggag gcggggtaga ggcggaaaca caacctgcag    120
ggccagagcg aggcgcgaga aggacggcgg cgtgaggggg cggggcgcgc agcgcgagaa    180
ggcaggcacg aggggcgagc gcgaggcggg gcacggcgcg tggcgtgaga cggggcgggg    240
cgcgcgtatc ggcgccgcgg ccgcgtgacg cgttttcaaa tcttcaaccg ccgcagccca    300
ctcgtttgtg cttttgcgcct tcctcctccg cgccttggag ccggatccgg ccccggaaac    360
ccgacctgca gacgcggtac ctctactgcg tagaggccgt agctggcgga aggagagagg    420
cggccgtcct gtcaacaggc cggggggaagc cgtgctttcg cggctgcccg gtgcgacact    480
ttctccggac ccagcatgta ggtgccgggc gactgccatg aactccggag ccatgaggat    540
ccacagtaaa ggacatttcc agggtggaat ccaagtcaaa aatgaaaaaa acagaccatc    600
tctgaaatct ctgaaaactg ataacaggcc agaaaaatcc aaatgtaagc cactttgggg    660
aaaagtattt taccttgact taccttctgt caccatatct gaaaaacttc aaaaggacat    720
taaggatctg ggagggcgag ttgaagaatt tctcagcaaa gatatcagtt atcttatttc    780
aaataagaag gaagctaaat ttgcacaaac cttgggtcga atttctcctg taccaagtcc    840
agaatctgca tatactgcag aaaccacttc acctcatccc agccatgatg gaagttcatt    900
taagtcacca gacacagtgt gtttaagcag aggaaaatta ttagttgaaa aagctatcaa    960
ggaccatgat tttattcctt caaatagtat attatcaaat gccttgtcat ggggagtaaa   1020
aattcttcat attgatgaca ttagatacta cattgaacaa aagaaaaaag agttgtatt     1080 actcaagaaa tcaagtactt cagtaagaga tgggggcaaa agagttggta gtggtgcaca    1140
aaaaacaaga acaggaagac tcaaaaagcc ttttgtaaag gtggaagata tgagccaaag    1200
ccctgcagtc catttgatgt agacaagcca tctagtatgc aaaagcaaac tcaggttaaa    1260
```

-continued

```
ctaagaatcc aaacagatgg cgataagtat ggtggaacct caattcaact ccagttgaaa   1320
gagaagaaga aaaaggata ttgtgaatgt tgcttgcaga aatatgaaga tctagaaact   1380
caccttctaa gtgagcaaca cagaaacttt gcacagagta accagtatca agttgttgat   1440
gatattgtat ctaagttagt ttttgacttt gtggaatatg aaaggacac acctaaaaag   1500 aaaagaataa aatacagtgt tggatcccctt tctcctgttt ctgcaagtgt cctgaaaaag   1560
actgaacaaa aggaaaaagt ggaattgcaa catatttctc agaaagattg ccaggaagat   1620
gatacaacag tgaaggagca gaatttcctg tataaagaga cccaggaaac tgaaaaaaag   1680
ctcctgttta tttcagagcc catcccccac ccttcaaatg aattgagagg cttaatgag   1740 aaaatgagta ataaatgttc catgttaagt acagctgaag atgacataag acagaatttt   1800
acacagctac ctctacataa aaacaaacag gaatgcattc ttgacatttc gaacacaca   1860 ttaagtgaaa atgacttaga agaactaagg gtagatcact ataaatgtaa catacaggca   1920
tctgtacatg tttctgattt cagtacagat aatagtggat ctcaaccaaa acagaagtca   1980
gatactgtgc ttttccagc aaaggatctc aaggaaaagg accttcattc aatatttact   2040
catgattctg gtctgataac aataaacagt tcacaagagc acctaactgt tcaggcaaag   2100
gctccattcc atactcctcc tgaggaaccc aatgaatgtg acttcaagaa tatggatagt   2160
ttaccttctg gtaaaataca tcgaaaagtg aaaataatat taggacgaaa tagaaaagaa   2220
aatctggaac caaatgctga atttgataaa agaactgaat ttattacaca agaagaaaac   2280
agaatttgta gttcaccggt acagtctttta ctagacttgt ttcagactag tgaagagaaa   2340
tcagaatttt tgggtttcac aagctacaca gaaaagagtg gtatatgcaa tgttttagat   2400
atttgggaag aggaaaattc agataatctg ttaacagcgt ttttctcgtc cccttcaact   2460
tctacattta ctggctttta gaatttaaaa aatgcatact tttcagaagt gataaggatc   2520
atattcttga aatttttata aatatgtatg gaaattctta ggattttttt accagctttg   2580
tttacagacc caaatgtaaa tattaaaaat aaatatttgc aatttctac agaattgaat   2640 acctgttaaa gaaaaattac agaataaact tgtgactggt cttgttttac attaaaaaaa   2700
aaaaaaaaaa aaactcgag   2719
```

<210> SEQ ID NO 5
<211> LENGTH: 67
<212> TYPE: PRT
<213> ORGANISM: Mus musculus

<400> SEQUENCE: 5

Leu Lys Ala Asp Asn Arg Leu Glu Lys Ser Lys Tyr Lys Pro Leu Met
1               5                   10                  15

Gly Lys Ile Phe Tyr Leu Asp Leu Pro Ser Ile Thr Ile Cys Glu Lys
            20                  25                  30

Leu Gln Lys Asp Ile Lys Glu Leu Gly Gly Arg Val Glu Glu Phe Leu
        35                  40                  45

Ser Lys Asp Ile Ser Tyr Phe Val Ser Asn Lys Lys Glu Ala Lys Tyr
    50                  55                  60

Ala Gln Thr
 65

<210> SEQ ID NO 6
<211> LENGTH: 66
<212> TYPE: PRT
<213> ORGANISM: Drosophila melanogaster

```
<400> SEQUENCE: 6

Thr Pro Pro Lys Val Lys Val Ile Lys Ser Lys Arg Pro Leu Cys His
 1               5                  10                  15

Phe Lys Phe Tyr Leu Asp Ile Cys Asp His Gln Leu Ala Lys Arg Ile
            20                  25                  30

Glu Ser Asp Ile Lys Ala Leu Gly Gly His Leu Glu Pro Phe Leu Ser
        35                  40                  45

Asp Asp Ile Thr His Phe Val Thr Asp Lys Pro Glu Val Ile Gly Gly
    50                  55                  60

Thr Ser
 65

<210> SEQ ID NO 7
<211> LENGTH: 59
<212> TYPE: PRT
<213> ORGANISM: Mus musculus

<400> SEQUENCE: 7

Lys Gln Ala Gln Pro Lys Leu Arg Ile Asn Met Asp Gly Asp Lys Cys
 1               5                  10                  15

Gly Thr Pro Val Gln Leu Gln Leu Lys Glu Lys Arg Lys Lys Gly Tyr
            20                  25                  30

Cys Glu Cys Cys Leu Gln Lys Tyr Glu Asp Leu Glu Thr His Leu Leu
        35                  40                  45

Ser Glu Lys His Arg Asn Phe Ala Gln Ser Asn
    50                  55

<210> SEQ ID NO 8
<211> LENGTH: 60
<212> TYPE: PRT
<213> ORGANISM: Drosophila melanogaster

<400> SEQUENCE: 8

Pro Ser Leu Gln Glu Leu Lys Lys Gln Ser Ala Ile Pro Asn Ser Pro
 1               5                  10                  15

Arg Ser Asn Cys Arg Glu Pro Ile Asp Ser Ser Glu Lys Gln Gly Gly
            20                  25                  30

Val Cys Glu Ile Cys Lys Leu Glu Tyr Asp Ile Leu Asn Ile His Leu
        35                  40                  45

Gln Ser Lys Asp His Glu Leu Phe Ala Lys Asn Ser
    50                  55                  60

<210> SEQ ID NO 9
<211> LENGTH: 59
<212> TYPE: PRT
<213> ORGANISM: Saccharomyces cerevisiae

<400> SEQUENCE: 9

Lys Lys Ser Thr Ser Thr Asn Val Thr Leu His Phe Asn Ala Gln Thr
 1               5                  10                  15

Ala Cys Thr Ala Gln Pro Val Lys Lys Glu Thr Val Lys Asn Ser Gly
            20                  25                  30

Tyr Cys Glu Asn Cys Arg Val Lys Tyr Glu Ser Leu Glu Gln His Ile
        35                  40                  45

Val Ser Glu Lys His Leu Ser Phe Ala Glu Asn
    50                  55
```